(12) United States Patent
McCormack et al.

(10) Patent No.: US 7,811,776 B2
(45) Date of Patent: Oct. 12, 2010

(54) USE OF VEGF-D IN THE DIAGNOSIS OF LYMPHANGIOLEIOMYOMATOSIS (LAM) DISEASE

(75) Inventors: Francis X. McCormack, Cincinnati, OH (US); Lisa R. Young, Cincinnati, OH (US)

(73) Assignees: University of Cincinnati, Cincinnati, OH (US); Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 12/328,727

(22) Filed: Dec. 4, 2008

(65) Prior Publication Data

US 2009/0156506 A1 Jun. 18, 2009

Related U.S. Application Data

(60) Provisional application No. 61/005,509, filed on Dec. 5, 2007.

(51) Int. Cl.
*G01N 33/53* (2006.01)
(52) U.S. Cl. .................. 435/7.1; 435/7.2; 435/7.91; 435/7.92
(58) Field of Classification Search .................. None
See application file for complete search history.

(56) References Cited

U.S. PATENT DOCUMENTS

| 6,383,484 B1 | 5/2002 | Achen et al. |
| 7,410,639 B2 | 8/2008 | Achen et al. |

FOREIGN PATENT DOCUMENTS

| WO | WO-98/07832 | 2/1998 |
| WO | WO-2005/087177 | 9/2005 |

OTHER PUBLICATIONS

Achen et al., Vascular endothelial growth factor D (VEGF-D) is a ligand for the tyrosine kinases VEGF receptor 2 (Flk1) and VEGF receptor 3 (Flt4), *Proc. Natl. Acad. Sci. USA*, 95: 548-53 (1998).

Berstein et al., How common are renal angiomyolipomas in patients with pulmonary lymphangiomyomatosis? *Am. J. Respir. Crit. Care. Med.*, 152: 2138-2143 (1995).

Byrum, Shellie; The LAM Foundation, Research sheds light on previously untreatable lung disease, Medical News Today News Article, www.medicalnewstoday.com, dated Jan. 11, 2008.

Carsillo et al., Mutations in the tuberous sclerosis complex gene TSC2 are a cause of sporadic pulmonary lymphangioleiomyomatosis, *Proc. Natl. Acad. Sci. USA*. 97: 6085-90 (2000).

Faul et al., Thoracic lymphangiomas, lymphangiectasis, lymphangiomatosis, and lymphatic dysplasia syndrome, *Am. J. Crit. Care Med.* 161: 1037-46 (2000).

Johnson et al., Lymphangioleiomyomatosis, *Eur. Respir. J.* 27: 1056-65 (2006).

Juvet et al., Molecular pathogenesis of lymphangioleiomyomatosis: lessons learned from orphans, *Am. J. Respir. Cell. Mol. Biol.* 36: 398-408 (2007).

McCormack et al., Lymphangioleiomyomatosis: A clinical update, *Chest*, 133: 507-16 (2008).

Ryu et al., Cystic and cavitary lung disease: Focal and diffuse, *Mayo Clin. Proc.* 78: 744-52 (2003).

Seyama et al., Vascular endothelial growth factor-D is increased in serum of patients with lymphangioleiomyomatosis, *Lymphat. Res. Biol.* 4: 143-52 (2006).

Stacker et al., Biosynthesis of vascular endothelial growth factor-D involves proteolytic processing which generates non-covalent homodimers, *J. Biol. Chem.* 247: 32127-36 (1999).

Young et al., Diagnostic potential of serum VEGF-D for lymphangioleiomyomatosis, *N. Engl. J. Med.* 358: 199-200 (2008).

Young et al., Serum VEGF-D as a Diagnostic Test for Lymphangioleiomyomatosis (LAM), Pulmonary, Critical Care, and Sleep Medicine, Cincinnati Children's Hospital Medical Center, *Am. J. Respir. Crit. Care Med.* 177: Poster to abstract A48 (2008).

Young et al., Lymphangioleiomyomatosis/Thematic Post Session, Serum VEGF-D as a Diagnostic Test for Lymphangioleiomyomatosis (LAM), *Am. J. Respir. Crit. Care Med.* 177: Abstracts issue: A130 (2008).

*Primary Examiner*—Jacob Cheu
(74) *Attorney, Agent, or Firm*—Marshall, Gerstein & Borun LLP

(57) ABSTRACT

Described herein are methods of diagnosing lymphangioleiomyomatosis (LAM) that permits differentiating LAM from another lung disorder. Methods of treatment are also provided.

29 Claims, 7 Drawing Sheets

SEQUENCE LISTING

<160> NUMBER OF SEQ ID NOS: 2

<210> SEQ ID NO 1
<211> LENGTH: 2029
<212> TYPE: DNA
<213> ORGANISM: Homo sapiens

<400> SEQUENCE: 1

```
gttgggttcc agctttctgt agctgtaagc attggtggcc acaccacctc cttacaaagc      60
aactagaacc tgcggcatac attggagaga ttttttttaat tttctggaca tgaagtaaat     120
```

```
ttagagtgct ttctaatttc aggtagaaga catgtccacc ttctgattat ttttggagaa      180
cattttgatt tttttcatct ctctctcccc acccctaaga ttgtgcaaaa aaagcgtacc      240
ttgcctaatt gaataatttt cattggattt tgatcagaac tgattatttg gttttctgtg      300
tgaagttttg aggtttcaaa ctttccttct ggagaatgcc ttttgaaaca attttctcta      360
gctgcctgat gtcaactgct tagtaatcag tggatattga aatattcaaa atgtacagag      420
agtgggtagt ggtgaatgtt ttcatgatgt tgtacgtcca gctggtgcag gctccagta       480 atgaacatgg accagtgaag cgatcatctc agtccacatt ggaacgatct gaacagcaga      540
tcagggctgc ttctagtttg gaggaactac ttcgaattac tcactctgag gactggaagc      600
tgtggagatg caggctgagg ctcaaaagtt ttaccagtat ggactctcgc tcagcatccc      660
atcggtccac taggtttgcg gcaactttct atgacattga aacactaaaa gttatagatg      720
aagaatggca agaactcagt gcagcccta gaaacgtg cgtggaggtg ccagtgagc          780 tggggaagag taccaacaca ttcttcaagc ccccttgtgt gaacgtgttc cgatgtggtg      840
gctgttgcaa tgaagagagc cttatctgta tgaacaccag cacctcgtac atttccaaac      900
agctctttga gatatcagtg cctttgacat cagtacctga attagtgcct gttaaagttg      960
ccaatcatac aggttgtaag tgcttgccaa cagcccccg ccatccatac tcaattatca      1020
gaagatccat ccagatccct gaagaagatc gctgttccca ttccaagaaa ctctgtccta      1080
ttgacatgct atgggatagc aacaaatgta atgtgttttt gcaggaggaa aatccacttg      1140
ctggaacaga agaccactct catctccagg aaccagctct ctgtgggcca cacatgatgt      1200
ttgacgaaga tcgttgcgag tgtgtctgta aaacaccatg tcccaaagat ctaatccagc      1260
accccaaaaa ctgcagttgc tttgagtgca agaaagtct ggagacctgc tgccagaagc      1320
acaagctatt tcacccagac acctgcagct gtgaggacag atgcccctttt cataccagac     1380 catgtgcaag tggcaaaaca gcatgtgcaa agcattgccg ctttccaaag agaaaaggg      1440 ctgcccaggg gccccacagc cgaaagaatc cttgattcag cgttccaagt tccccatccc      1500
tgtcattttt aacagcatgc tgctttgcca agttgctgtc actgttttt tcccaggtgt       1560 taaaaaaaa atccatttta cacagcacca cagtgaatcc agaccaacct tccattcaca      1620
ccagctaagg agtccctggt tcattgatgg atgtcttcta gctgcagatg cctctgcgca      1680
ccaaggaatg gagaggaggg gacccatgta atccttttgt ttagttttgt ttttgtttt      1740 tggtgaatga gaaaggtgtg ctggtcatgg aatggcaggt gtcatatgac tgattactca     1800
gagcagatga ggaaaactgt agtctctgag tcctttgcta atcgcaactc ttgtgaatta     1860
ttctgattct ttttttatgca gaatttgatt cgtatgatca gtactgactt tctgattact   1920
gtccagctta tagtcttcca gtttaatgaa ctaccatctg atgtttcata tttaagtgta    1980
tttaaagaaa ataaacacca ttattcaagc caaaaaaaa aaaaaaaa                    2029
```

<210> SEQ ID NO 2
<211> LENGTH: 354
<212> TYPE: PRT
<213> ORGANISM: Homo sapiens

<400> SEQUENCE: 2

Met Tyr Arg Glu Trp Val Val Asn Val Phe Met Met Leu Tyr Val
1               5                   10                  15

Gln Leu Val Gln Gly Ser Ser Asn Glu His Gly Pro Val Lys Arg Ser
            20                  25                  30

Ser Gln Ser Thr Leu Glu Arg Ser Glu Gln Gln Ile Arg Ala Ala Ser

```
                        35                      40                      45
Ser Leu Glu Glu Leu Leu Arg Ile Thr His Ser Glu Asp Trp Lys Leu
    50                      55                      60

Trp Arg Cys Arg Leu Arg Leu Lys Ser Phe Thr Ser Met Asp Ser Arg
65                      70                      75                      80

Ser Ala Ser His Arg Ser Thr Arg Phe Ala Ala Thr Phe Tyr Asp Ile
                85                      90                      95

Glu Thr Leu Lys Val Ile Asp Glu Glu Trp Gln Arg Thr Gln Cys Ser
                100                     105                     110

Pro Arg Glu Thr Cys Val Glu Val Ala Ser Glu Leu Gly Lys Ser Thr
                115                     120                     125

Asn Thr Phe Phe Lys Pro Pro Cys Val Asn Val Phe Arg Cys Gly Gly
        130                     135                     140

Cys Cys Asn Glu Glu Ser Leu Ile Cys Met Asn Thr Ser Thr Ser Tyr
145                     150                     155                     160

Ile Ser Lys Gln Leu Phe Glu Ile Ser Val Pro Leu Thr Ser Val Pro
                165                     170                     175

Glu Leu Val Pro Val Lys Val Ala Asn His Thr Gly Cys Lys Cys Leu
                180                     185                     190

Pro Thr Ala Pro Arg His Pro Tyr Ser Ile Ile Arg Arg Ser Ile Gln
                195                     200                     205

Ile Pro Glu Glu Asp Arg Cys Ser His Ser Lys Lys Leu Cys Pro Ile
        210                     215                     220

Asp Met Leu Trp Asp Ser Asn Lys Cys Lys Cys Val Leu Gln Glu Glu
225                     230                     235                     240

Asn Pro Leu Ala Gly Thr Glu Asp His Ser His Leu Gln Glu Pro Ala
                245                     250                     255

Leu Cys Gly Pro His Met Met Phe Asp Glu Asp Arg Cys Glu Cys Val
                260                     265                     270

Cys Lys Thr Pro Cys Pro Lys Asp Leu Ile Gln His Pro Lys Asn Cys
            275                     280                     285

Ser Cys Phe Glu Cys Lys Glu Ser Leu Glu Thr Cys Cys Gln Lys His
        290                     295                     300

Lys Leu Phe His Pro Asp Thr Cys Ser Cys Glu Asp Arg Cys Pro Phe
305                     310                     315                     320

His Thr Arg Pro Cys Ala Ser Gly Lys Thr Ala Cys Ala Lys His Cys
                325                     330                     335

Arg Phe Pro Lys Glu Lys Arg Ala Ala Gln Gly Pro His Ser Arg Lys
                340                     345                     350

Asn Pro
```

USE OF VEGF-D IN THE DIAGNOSIS OF LYMPHANGIOLEIOMYOMATOSIS (LAM) DISEASE

CROSS-REFERENCE TO RELATED APPLICATION

The present application is based on U.S. Provisional Application No. 61/005,509, filed Dec. 5, 2007, the disclosure of which is incorporated herein by reference in its entirety.

BACKGROUND OF THE INVENTION

Lymphangioleiomyomatosis (LAM) is a rare lung disease that affects almost exclusively women, which occurs in the presence and absence of tuberous sclerosis complex (TSC-LAM) or sporadic (S-LAM), respectively. LAM is characterized by an unusual type of muscle cell that invades the tissue of the lungs, including the airways, and blood and lymph vessels. Over time, these muscle cells form into bundles and grow into the walls of the airways, and blood and lymph vessels, causing them to become obstructed.

Although these muscle cells are not considered cancerous, they grow without the usual controls within the lungs. Over time, the muscle cells block the flow of air, blood, and lymph vessels to and from the lungs, preventing the lungs from providing oxygen to the rest of the body.

The most common presentation of LAM is progressive dyspnea on exertion, often in association with a history of pneumothorax or chylothorax (other symptoms of LAM include chest pain and coughing). The histopathological hallmarks of the disease are dilated distal airspaces and diffuse infiltration of the pulmonary interstitium with atypical smooth muscle cells, including spaces surrounding airways, vessels, and lymphatics. The differential diagnosis of the thin walled cystic change that is characteristic of LAM also includes emphysema, pulmonary Langerhan's cell histiocytosis (PLCH), lymphocytic interstitial pneumonitis, Birtt Hogg Dubé syndrome, and Sjogren's syndrome. Rare syndromes of benign or malignant smooth muscle metastasis may also produce cystic change and closely mimic LAM, including benign metastasizing leiomyoma, endometrial stromal sarcomas, and low-grade leiomyosarcomas. Classical methods of diagnosing LAM disease include chest X-rays, high-resolution CT scans and lung biopsies (e.g., thoracoscopy, open biopsy and transbronchial biopsy).

Because many of the early signs and symptoms of lymphangioleiomyomatosis (LAM) are similar to those of other lung diseases, including asthma, emphysema and bronchitis, LAM can be difficult to diagnose. Thus, there remains a need in the art for a diagnostic assay to differentiate LAM disease from other respiratory disorders.

SUMMARY OF THE INVENTION

The present invention is directed to the use of VEGF-D in a diagnostic assay to differentiate lymphangioleiomyomatosis (LAM) from other respiratory disorders.

In one aspect, the invention provides a method of diagnosis of LAM that permits differentiating LAM from another lung disorder comprising determining VEGF-D concentration in a biological sample from a human subject that has tuberous sclerosis complex (TSC), a cystic or a chylous lung disorder, and diagnosing the presence or absence of LAM from the VEGF-D concentration, wherein LAM correlates with elevated VEGF-D concentration in the sample, compared to VEGF-D concentration in subjects with TSC, a cystic or chylous lung disorder that are free of LAM.

The term "cystic lung disorder" as used herein means a disorder characterized by a clearly defined air-containing space surrounded by a relatively thin ($\leq 4$ mm) wall in the lung of a subject. Exemplary cystic lung disorders include, but are not limited to lymphangiomatosis, Pulmonary Langerhan's cell histiocytosis (PLCH), emphysema, Sjögren'syndrome with cystic lung disease, Birtt-Hogg-Dubé syndrome, follicular bronchitis, lymphocytic interstitial pneumonitis, hypersensitivity pneumonitis, amyloidosis, light chain-deposition disease, lymphoma, bronchopulmonary dysplasia, metastatic endometrial cell sarcoma, synovial cell sarcoma, low-grade leiomyosarcoma, other metastatic malignancies that produce thin walled pulmonary cysts such as genitourinary cancers, barotrauma, smoking related cystic changes, pneumocystis with pneumatoceles.

The term "chylous lung disorder" as used herein means a disorder characterized by the accumulation of chyle in the pleural space or abdomen of a subject with a lung disorder. Exemplary chylous disorders include, but are not limited to, chylothorax, chylous ascites, lymphangiectasia, chyloperi-cardium, and lymphangioma.

In another aspect, the invention provides a method of diagnosis comprising: diagnosing the presence of a TSC, a cystic or chylous lung disorder in a human subject determining VEGF-D concentration in a biological sample from said subject; and diagnosing the presence or absence of LAM from the VEGF-D concentration, wherein LAM correlates with elevated VEGF-D concentration in the sample compared to VEGF-D in subjects with TSC, a cystic or a chylous lung disorder that are free of LAM. In some embodiments, the sample comprises serum from the subject. In some embodiments, the human subject is female.

In some embodiments, the subject has TSC. In some embodiments, the LAM is selected from the group consisting of tuberous sclerosis complex lymphangioleiomyomatosis (TSC-LAM) and non-heritable sporadic form lymphangioleiomyomatosis (S-LAM).

In some embodiments, a serum VEGF-D concentration greater than 574 pg/ml in the biological sample is identified as elevated. In other embodiments, a serum VEGF-D concentration greater than 750 pg/ml in the biological sample is identified as elevated.

In some embodiments, the methods described herein further comprise obtaining a computer tomography (CT) scan of a lung from the subject, wherein the diagnosing is based on the VEGF-D concentration and the CT scan.

In some embodiments, the methods described herein further comprise obtaining a lung biopsy, wherein the diagnosing is based on the VEGF-D concentration and the lung biopsy.

Another aspect of the invention provides a method of differentiating LAM from TSC or a cystic or chylous lung disorder comprising obtaining a measurement of VEGF-D from a human subject; and differentiating LAM from TSC or a cystic or chylous lung disorder by comparing the level of VEGF-D in the sample to a predetermined criterion.

In some embodiments, the predetermined criterion is a measure of VEGF-D in healthy human controls, wherein VEGF-D in LAM is elevated compared to the controls. In some embodiments, the predetermined criterion is a measure of VEGF-D in humans with LAM. In some embodiments, the predetermined criterion is a receiver operating characteristic curve based on data of VEGF-D measurements in subjects with LAM and subjects with TSC or a cystic or chylous lung disorder that are free of LAM. In still other embodiments, the predetermined criterion is a cutoff value of VEGF-D concentration, wherein the cutoff value is determined, based on previous measurements to discriminate LAM with a sensitivity and specificity calculated from measurements of VEGF-D in human subjects with LAM and human subjects with TSC or a cystic or chylous lung disorder that are free of LAM. In some embodiments, the measurement of VEGF-D is a serum concentration and the cutoff value is about 574 pg/mL. In other embodiments, the measurement of VEGF-D is a serum concentration and the cutoff value is about 750 pg/mL.

In some embodiments, the human subjects free of LAM have at least one cystic or chylous disorder selected from the group consisting of lymphangiomatosis, Pulmonary Langerhan's cell histiocytosis (PLCH) emphysema, Sjögren's syndrome and Birtt-Hogg-Dubé syndrome. In some embodiments, the human subjects free of LAM have TSC.

In some embodiments, the obtaining a measurement step described herein comprises contacting the sample with a VEGF-D antibody under conditions that allow binding of the antibody (e.g., monoclonal antibody and antigen-binding fragment), to VEGF-D in the sample. In some embodiments, the measurement is obtained from serum of the subject. In some embodiments, the obtaining step further comprises quantitatively determining the amount of antibody-VEGF-D complex formed. In some embodiments, an ELISA assay is used to measure the VEGF-D.

In some embodiments, the antibody is immobilized on a solid support. In some embodiments, the antibody is labeled, and the amount of VEGF-D is determined my measuring the amount of label in antibody-VEGF-D complex.

Another aspect of the invention provides methods of predicting whether a human subject with TSC, or a cystic or chylous lung disorder has LAM. Such methods comprise determining VEGF-D concentration in a biological sample from the subject and predicting whether the subject has LAM from the VEGF-D concentration. In some embodiments, the predicting step comprises comparing the VEGF-D concentration in the sample to a predetermined criterion described herein.

Another aspect of the invention provides a method of treating LAM in a subject comprising diagnosing a subject as having LAM according to the method described herein; and administering a standard of care therapeutic to the subject.

Also provided is the use of a VEGF-D antibody for screening a subject with TSC or a cystic or chylous lung disorder to determine whether the subject has LAM disease.

In another aspect, the invention embraces a diagnostic test system comprising means for obtaining test results comprising the level of VEGF-D in at least one biological sample; means for collecting and tracking test results for one or more individual biological sample; means for comparing the level of VEGF-D to a predetermined criterion; and means for reporting whether the level of VEGF-D meets or exceeds the predetermined criterion. The means for collecting and tracking test results for one or more individuals can comprise a data structure or database. The means for reporting whether the level of VEGF-D meets or exceeds the predetermined criterion can comprise a visible display, an audio output, a link to a data structure or database, or a printer.

A "diagnostic system" is any system capable of carrying out the methods of the invention, including computing systems, environments, and/or configurations that may be suitable for use with the methods or system of the claims include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

Still another embodiment of the invention is a computer readable medium having computer executable instructions for differentiating LAM from TSC or a cystic or chylous lung disorder, the computer readable medium comprising: a routine, stored on the computer readable medium and adapted to be executed by a processor, to store a predetermined criterion or (predetermined criteria); and a routine stored on the computer readable medium and adapted to be executed by a processor to compare the amount of VEGF-D in a test sample data to a predetermined criterion to differentiate LAM from TSC or a cystic or chylous lung disorder.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations defined by specific paragraphs above. For example, certain aspects of the invention that are described as a genus, and it should be understood that every member of a genus is, individually, an aspect of the invention. Also, aspects described as a genus or selecting a member of a genus, should be understood to embrace combinations of two or more members of the genus. Although the applicant(s) invented the full scope of the invention described herein, the applicants do not intend to claim subject matter described in the prior art work of others. Therefore, in the event that statutory prior art within the scope of a claim is brought to the attention of the applicant(s) by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

DETAILED DESCRIPTION

Figure 1:
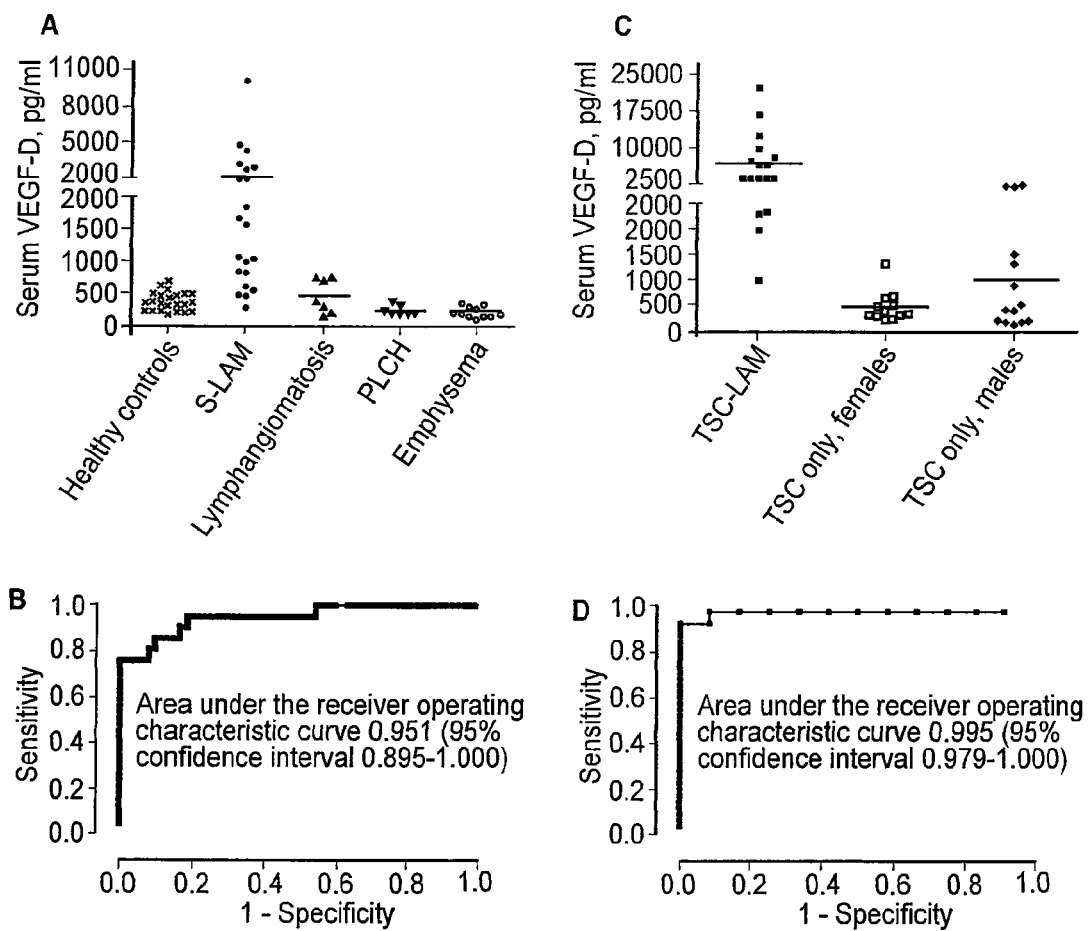
FIG. 1A shows VEGF-D serum levels in healthy controls, S-LAM patients, PLCH patients, lymphangiomatosis patients and emphysema patients.
FIG. 1B shows a receiver operating characteristic (ROC) curve for various cutoff levels of VEGF-D in differentiating between S-LAM and healthy and other disease controls (i.e., PLCH patients, lymphangiomatosis patients and emphysema patients).
FIG. 1C shows VEGF-D serum levels in TSC-LAM, females with TSC (without LAM) and males with TSC (without LAM).
FIG. 1D shows a ROC curve for various cutoff levels of VEGF-D in differentiating between females with TSC-LAM and females with TSC (without LAM).

It has been discovered that the level of Vascular Endothelial Growth Factor-D (VEGF-D) in a sample of a subject is a useful tool for differentiating LAM disease from other respiratory disorders (including TSC and a chylous or cystic lung disorder).

VEGF-D

The growth factor VEGF-D, as well as human sequences encoding VEGF-D, and VEGF-D variants and analogs, have been described in detail in International Patent Application Number PCT/US97/14696, filed Aug. 21, 1997 and published on Feb. 26, 1998 as International Publication Number WO 98/07832; and in Achen, et al., Proc. Nat'l Acad. Sci. U.S.A., 95(2): 548-553 (1998), both incorporated herein by reference in the entirety. VEGF-D was isolated as an incomplete fragment from a human breast cDNA library, commercially available from Clontech, by screening with an expressed sequence tag obtained from a human cDNA library designated "Soares Breast 3NbHBst" as a hybridization probe (Achen et al., supra). Full length VEGF-D was subsequently cloned from a human lung cDNA library (WO98/07832). As explained therein in detail, human VEGF-D is initially produced in human cells as a prepro-VEGF-D polypeptide of 354 amino acids. A cDNA and deduced amino acid sequence for human prepro-VEGF-D are set forth in SEQ ID NOs: 1 and 2, respectively. VEGF-D sequences from other species also have been reported. See Genbank Accession Nos. D89628 (Mus musculus); and AF014827 (Rattus norvegicus), for example, incorporated herein by reference.

VEGF-D is initially expressed as a prepro-peptide that undergoes N-terminal and C-terminal proteolytic processing, and forms non-covalently linked dimers. VEGF-D stimulates mitogenic responses in endothelial cells in vitro. During embryogenesis, VEGF-D is expressed in a complex temporal and spatial pattern, and its expression persists in the heart, lung, and skeletal muscles in adults. Isolation of a biologically active fragment of VEGF-D designated VEGF-DΔNΔC, is described in International Patent Publication No. WO 98/07832, the disclosure of which is incorporated herein by reference.

The prepro-VEGF-D polypeptide has a putative signal peptide of 21 amino acids and is apparently proteolytically processed in a manner analogous to the processing of prepro-VEGF-C. A "recombinantly matured" VEGF-D, VEGF-DΔNΔC, containing amino acid residues 93 to 201, and lacking residues 1-92 and 202-354 of SEQ ID NO: 2 retains the ability to activate receptors VEGFR-2 and VEGFR-3, and appears to associate as non-covalently linked dimers. Thus, preferred VEGF-D polynucleotides include those polynucleotides that comprise a nucleotide sequence encoding amino acids 93-201 of SEQ ID NO: 2.

The predominant intracellular form of human VEGF-D is a homodimeric propeptide that consists of the VEGF/PDGF Homology Domain (VHD) and the N- and C-terminal propeptides. After secretion, this polypeptide is proteolytically cleaved (Stacker et al., J Biol Chem 274:32127-32136, 1999). The human VEGF-D VHD consists of residues 93 to 201 of full length VEGF-D and contains the binding sites for both VEGFR-2 and VEGFR-3.

The description of the cloning of the mouse homolog of VEGF-D is also found in Intl. Patent Application PCT/U.S. 97/14696 (WO 98/07832).

Antibodies to VEGF-D are described below in greater detail.

Diagnostic Methods

In one aspect, the invention provides a method of diagnosis of LAM that permits differentiating LAM from another lung disorder comprising determining VEGF-D concentration in a biological sample from a human subject that has TSC or a cystic or chylous lung disorder, and diagnosing the presence or absence of LAM from the VEGF-D concentration, wherein LAM correlates with elevated VEGF-D concentration in the sample, compared to VEGF-D concentration in subjects with TSC or a cystic or chylous lung disorder that is free of LAM. In another aspect, the invention provides a method of diagnosis comprising diagnosing the presence of TSC or a cystic or chylous lung disorder in a human subject; determining VEGF-D concentration in a biological sample from said subject; and diagnosing the presence or absence of LAM from the VEGF-D concentration, wherein LAM correlates with elevated VEGF-D concentration in the sample compared to VEGF-D in subjects with TSC or a cystic or chylous lung disorder that are free of LAM.

In some embodiments, a VEGF-D concentration greater than 488 pg/mL, greater than 490 pg/mL, greater than 500 pg/mL, greater than 510 pg/mL, greater than 520 pg/mL, greater than 530 pg/mL, greater than 540 pg/mL, greater than 550 pg/mL, greater than 560 pg/mL, greater than 570 pg/mL, greater than 580 pg/mL, greater than 590 pg/mL, greater than 600 pg/mL, greater than 610 pg/mL, greater than 620 pg/mL, greater than 630 pg/mL, greater than 640 pg/mL, greater than 650 pg/mL, greater than 660 pg/mL, greater than 670 pg/mL, greater than 680 pg/mL, greater than 690 pg/mL, greater than 700 pg/mL, greater than 710 pg/mL, greater than 720 pg/mL, greater than 730 pg/mL, greater than 740 pg/mL, greater than 750 pg/mL, greater than 760 pg/mL, greater than 770 pg/mL, greater than 780 pg/mL, greater than 790 pg/mL, or greater than 800 pg/mL, in the biological sample is identified as elevated and indicative of LAM. In some embodiments, a VEGF-D concentration of 574 pg/ml in the biological sample is indicative of LAM. In some embodiments, a VEGF-D concentration greater than 750 pg/ml in the biological sample is indicative of LAM. VEGF-D concentration in the range defined by any of these cut-off points is indicative of LAM. The Examples herein demonstrate how adjustment of the diagnostic cut-off value will achieve different levels of sensitivity or specificity as desired.

Also provided is a method of differentiating LAM from another respiratory disorder comprising obtaining a measurement of VEGF-D from a human subject; and differentiating LAM from another respiratory disorder by comparing the level of VEGF-D in the sample to a predetermined criterion.

The term "predetermined criterion" as used herein refers to measure of serum VEGF-D obtained from samples from a plurality of subjects. In some variations, the predetermined criterion is a measure of VEGF-D in healthy human controls (i.e., subjects with no clinical manifestation of any respiratory disorder), in which case VEGF-D in LAM is elevated compared to the predetermined criterion from the healthy controls. In other variations, the predetermined criterion is a measure of VEGF-D in humans with LAM, which might include information such as mean, standard deviation, quartile measurements, confidence intervals, or other information about the distribution or range of VEGF-D concentration in LAM subjects. In still other variations, the predetermined criterion is a receiver operating characteristic curve based on data of VEGF-D measurements in subjects with LAM and subjects free of LAM. In still other variations, the predetermined criterion is a cutoff value of VEGF-D concentration, wherein the cutoff value is determined, based on previous measurements to discriminate LAM with a sensitivity and specificity calculated from measurements of VEGF-D in human subjects with LAM and human subjects free of LAM. Optionally, the predetermined criterion is based on subjects further stratified by other characteristics that can be determined for a subject, to further refine the diagnostic precision. Such additional characteristics include, for example, sex, age, weight, smoking habits, race or ethnicity, blood pressure, other diseases, and medications (e.g., anti-inflammatory agents, cardiovascular medications and anti-neoplastic medications).

In some embodiments, the predetermined criterion is a measurement obtained from samples from a plurality of subjects that do not have LAM (e.g., healthy human controls; TSC patients (without LAM); lymphangiomatosis patients; emphysema patients; PLCH patients; Sjogren's Syndrome patients; and Birtt-Hogg-Dubé syndrome patients). In such embodiments, the predetermined criterion corresponds to the level (or concentration) of serum VEGF-D obtained from a plurality of subjects that do not have LAM. For example, in one study, levels of serum VEGF-D in healthy human controls range from about 150 pg/mL to about 689 pg/mL (mean±SD: 353±138 pg/mL); levels of serum VEGF-D in women TSC patients without LAM range from about 244 pg/mL to about 1,356 pg/mL (mean±SD: 491±315 pg/mL); levels of serum VEGF-D in lymphangiomatosis patients range from about 137 pg/mL to about 751 pg/mL (mean±SD: 457±270 pg/mL); levels of serum VEGF-D in PLCH patients range from about 163 pg/mL to about 383 pg/mL (mean±SD: 243±77 pg/mL); levels of serum VEGF-D in emphysema patients range from about 136 pg/mL to about 375 pg/mL (mean±SD: 236±74 pg/mL); and levels of serum VEGF-D in Sjorgen's Syndrome patients range from about 179 pg/mL to about 308 pg/mL (mean±SD: 240±65 pg/mL). in one study, levels of serum VEGF-D in male TSC patients (without LAM) patients range from about 179 pg/mL to about 3045 pg/mL (mean±SD: 1033±1033 pg/mL). In one study, the level of serum VEGF-D in a Birtt-Hogg-Dubé patient was 307 pg/mL.

In some embodiments, the predetermined criterion is a measurement obtained from samples from a plurality of subjects that have LAM (e.g., S-LAM and TSC-LAM). In such embodiments, the predetermined criterion corresponds to the level (or concentration) of serum VEGF-D obtained from a plurality of subjects that have LAM (e.g., S-LAM and TSC-LAM). For example, in one study, levels of serum VEGF-D in S-LAM patients range from about 274 pg/mL to about 10,092 pg/mL (mean±SD: 2118±2225 pg/mL); and levels of serum VEGF-D in TSC-LAM patients range from about 996 pg/mL to about 22,376 pg/mL (mean±SD: 6804±5791 pg/mL). In one study, levels of serum VEGF-D in male TSC-LAM patients were 973 pg/mL and 2,707 pg/mL.

In some embodiments, the methods described herein further comprise obtaining a computer tomography (CT) scan of a lung from the subject and the diagnosing is based on the VEGF-D concentration and the CT scan. In some embodiments, the CT scan is reviewed by at least two radiologists and the diagnosing is based on the VEGF-D concentration and the CT scan. For example, in some embodiments, the methods described herein further comprise evaluating a high resolution computer tomography (HRCT) or other medical imaging scan of the chest of the subject. The HRCT scan of a LAM subject will reveal cysts or abnormal clusters of cells in the lungs, of the subject, a collapsed lung or enlarged lymph nodes. The HRCT will also show the extent to which the cysts have spread.

Subjects with LAM characteristically show numerous thin-walled lung cysts, surrounded by relatively normal lung parenchyma. These cysts generally range from 2 mm to 5 cm in diameter, but can be larger. Their size tends to increase with progression of the disease. In some cases, a slight increase in linear interstitial markings, interlobular septal thickening, or patchy areas of ground glass opacity are also seen. Other features of LAM that can be seen on CT include hilar, mediastinal, and retrocrural adenopathy. Pleural effusion can also be seen, and can be helpful in distinguishing LAM from Langerhans cell histiocytosis In some embodiments, the methods described herein further comprises evaluating an abdominal CT scan of the subject. An abdominal CT scan is also recommended, as benign kidney tumors, known as angiomyolipomas, are found in 40% of women with LAM. See also Bernstein, et al., Am. J. Respir. Crit. Care Med. 152:2138-2143, 1995.

In some embodiments, the methods described herein further comprise obtaining a lung biopsy, wherein the diagnosing is based on the VEGF-D concentration and the lung biopsy. Lung biopsies of a LAM patient will reveal smooth muscle cell infiltration and cystic destruction in the lung tissue, as well as positive staining with human melanoma black (HMB)-45 antibody.

Methods for Measuring VEGF-D in a Sample

Preferred methods for measuring VEGF-D employ an agent that binds VEGF-D with great specificity and binding affinity, to permit measurements of VEGF-D that are typically in the picogram per mL range. Although exemplified with antibodies, other suitable binding reagents exist and can be used to practice the invention.

In some embodiments, a VEGF-D antibody is used to measure the amount of VEGF-D in a sample. To determine the presence or absence of LAM, a biological sample from a human subject is contacted with a VEGF-D antibody under conditions and for a time sufficient to allow immunocomplexes to form. Immunocomplexes formed between a VEGF-D antibody and VEGF-D in the sample are then detected. The amount of VEGF-D in the biological sample is quantitated by measuring the amount of the immunocomplex formed between the antibody and VEGF-D. For example, the capture antibody can be quantitatively measured if it has a detectable label, or a secondary antibody can be used to quantify the immunocomplex The biological samples of the present invention include biological fluids such as sputum, blood, serum, chylous fluids, urine bronchoalveolar lavage fluid, pleural effusions, ascites fluid, tracheal aspirate, saliva, or plasma. The sample may be processed prior to analysis, e.g., isolation of serum or plasma from a blood sample, and/or concentration or dilution to facilitate measurement. The sample also may be obtained from the lungs, e.g., a bronchioalveolar lavage (BAL) fluid sample may be used. In some embodiments, a biological sample is isolated from a human subject and is incubated with a VEGF-D antibody, and the level of the antibody-VEGF-D complex above a predetermined criterion or cut-off is correlated with the presence of LAM, and a level below said criterion or cut-off indicates that the subject is unlikely to have LAM. For example, a level of serum VEGF-D within the normal range indicates the subject is unlikely to have LAM.

Conditions for incubating an antibody with a sample vary. Incubation conditions depend on the format employed in the assay, the detection methods employed, and the type and nature of the antibody used in the assay. Commonly available immunological assay formats can readily be adapted to measure VEGF-D antibodies to practice the methods described herein. Suitable assays are well known in the art and are amply described in the scientific and patent literature (Harlow, Edward, and David Lane. *Using Antibodies: A Laboratory Manual*. Cold Spring Harbor, N.Y.: Cold Spring Harbor Laboratory Press, 1999, or more recent editions; Immunoassays: A Practical Approach, Oxford University Press, Gosling, J. P. (ed.) (2001) or more recent editions; and/or Current Protocols in Molecular Biology (Ausubel et al.), which is regularly updated). Exemplary assays include, but are not limited to, the double monoclonal antibody sandwich immunoassay technique (U.S. Pat. No. 4,376,110); monoclonal-polyclonal antibody sandwich assays (Wide et al., 1970); the "western blot" method (U.S. Pat. No. 4,452,901); immunoprecipitation of labeled ligand (Brown et al., 1980); enzyme-linked immunosorbent assays (Raines and Ross, 1982); immunocytochemical techniques, including the use of fluorochromes (Brooks et al., 1980); and neutralization of activity (Bowen-Pope et al., 1984). Other immunoassays include, but are not limited to, those described in U.S. Pat. Nos. 3,817,827; 3,850,752; 3,901,654; 3,935,074; 3,984,533; 3,996,345; 4,034,074; and 4,098,876; Chard, T., An Introduction to Radioimmunoassay and Related Techniques, Elsevier Science Publishers, Amsterdam, The Netherlands (1986); Bullock, G. R. et al., Techniques in Immunocytochemistry, Academic Press, Orlando, Fla. Vol. 1(1982), Vol. 2 (1983), Vol. 3 (1985); Tijssen, P., Practice and Theory of immunoassays: Laboratory Techniques in Biochemistry and Molecular Biology, Elsevier Science Publishers, Amsterdam, The Netherlands (1985).

For detection purposes, a VEGF-D antibody may either be labeled or unlabeled. Unlabeled antibodies may be used in agglutination assays or in combination with labeled detection reagents that bind to the immunocomplexes (e.g., anti-immunoglobulin, protein G, Protein A or a lectin and secondary antibodies, or antigen-binding fragments thereof, capable of binding to the antibodies that specifically bind to the VEGF-D). If the VEGF-D antibody is labeled, the reporter group may be any suitable reporter group known in the art, including radioisotopes, fluorescent groups (e.g. fluorescein or rhodamine), luminescent groups, enzymes, biotin and dye particles. Labels that are themselves directly detectable include fluorescent or luminescent dyes, metals or metal chelates, electrochemical labels, radionuclides (e.g., $^{32}$P, $^{14}$C, $^{125}$I, $^{3}$H, or $^{131}$I), magnetic labels or beads (e.g., DYNABEADS), paramagnetic labels, or colorimetric labels (e.g., colloidal gold, colored glass or plastic beads). Such detectable labels may be directly conjugated to the VEGF-D antibody or detection reagent or may be associated with a bead or particle that is attached to the VEGF-D antibody or detection reagent. Labels that are detectable through binding of a labeled specific binding partner include, but are not limited to, biotin, digoxigenin, maltose, oligohistidine, 2,4-dinitrobenzene, phenylarsenate, ssDNA, or dsDNA). Indirect labels that can be indirectly detected by their production of a detectable reaction product include various enzymes well known in the art, such as alkaline phosphatase, horseradish peroxidase, β-galactosidase, xanthine oxidase, glucose oxidase or other saccharide oxidases, or luciferases, which cleave appropriate substrate to form a colored or fluorescent reaction product.

Within certain assays, an unlabeled VEGF-D antibody is immobilized on a solid support, for use as a "capture agent" (or reagent) that captures the VEGF-D within a biological sample. Exemplary assays include Biacore and Surface Plasmon Resonance (SPR). The solid support may be any material known to those of ordinary skill in the art to which the antibody may be attached. For example, the solid support is a test well in a microtiter plate or a nitrocellulose or other suitable membrane. Alternatively, the solid support is a tube, bead, particle or disc, such as glass, fiberglass, latex or a plastic material such as polyethylene, polypropylene, polystyrene or polyvinylchloride or a porous matrix. Other materials include agarose, dextran, polyacrylamide, nylon, Sephadex, cellulose or polysaccharides. The solid support may also be a magnetic particle or a fiber optic sensor, such as those disclosed, for example, in U.S. Pat. No. 5,359,681. The immobilized VEGF-D antibody may be a polyclonal antibody, a monoclonal antibody, or a combination of polyclonal and monoclonal antibodies. The antibody may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is contemplated. In such cases, adsorption may be achieved by contacting the VEGF-D antibody, in a suitable buffer, with the solid support for a suitable amount of time.

Following immobilization, the remaining protein binding sites on the support are typically blocked. Any suitable blocking agent known to those of ordinary skill in the art, including bovine serum albumin, Tween™ 20™ (Sigma Chemical Co., St. Louis, Mo.), heat-inactivated normal goat serum (NGS), or BLOTTO (buffered solution of nonfat dry milk which also contains a preservative, salts, and an antifoaming agent) can be used. The support is then incubated with a biological sample. The sample can be applied neat, or, more often, it can be diluted, usually in a buffered solution which contains a small amount (0.1%-5.0% by weight) of protein, such as BSA, NGS, or BLOTTO. In general, an appropriate contact time (i.e., incubation time) is a period of time that is sufficient to detect the presence of antibody or an antigen binding fragment that is immunospecific for the VEGF-D within a sample. Preferably, the contact time is sufficient to achieve a level of binding that is at least about 95% of that achieved at equilibrium between bound and unbound antibody or antibody fragment. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween™ 20. A detection reagent that binds to the VEGF-D in the immunocomplexes (formed by binding of the capture agent and the VEGF-D from the sample) or that binds the complex may then be added. Such detection reagent may be a polyclonal antibody, or a monoclonal antibody, or a combination of polyclonal and monoclonal antibodies or an antigen binding fragment thereof. The detection reagent may be directly labeled, i.e., comprises at least a first detectable label or "reporter" molecule. Alternatively, the detection reagent may be an unlabeled VEGF-D antibody. This unlabeled VEGF-D (primary) antibody is then detected by the binding of a labeled secondary antibody or reagent to the primary antibody. For example, if the primary antibody is a murine immunoglobulin, the secondary antibody may be a labeled anti-murine immunoglobulin antibody. Similarly, if the primary antibody is a rabbit immunoglobulin, the secondary antibody may be a labeled anti-rabbit immunoglobulin antibody.

The detection reagent is incubated with the immunocomplex for an amount of time sufficient to detect the bound antibody or antigen binding fragment thereof. An appropriate amount of time may generally be determined by assaying the level of binding that occurs over a period of time. Unbound label or detection reagent is then removed and bound label or detection reagent is detected using a suitable assay or analytical instrument. The method employed for detecting the reporter group depends upon the nature of the reporter group. For radioactive labels, scintillation counting or autoradiographic methods are generally appropriate. Spectroscopic methods may be used to detect dyes, luminescent or chemiluminescent moieties and various chromogens, fluorescent labels and such like. Biotin may be detected using avidin, coupled to a different reporter group (commonly a radioactive or fluorescent group or an enzyme). Enzyme reporter groups (including horseradish peroxidase, β-galactosidase, alkaline phosphatase and glucose oxidase) may generally be detected by the addition of substrate (generally for a specific period of time), followed by spectroscopic or other analysis of the reaction products.

In alternative embodiments, the sample and detection reagent may be contacted simultaneously with the capture agent, rather than sequentially added. In yet another alternative, the sample and detection reagent may be pre-incubated together, then added to the capture agent. Other variations are readily apparent to one of ordinary skill in the art.

In some embodiments, VEGFR-2 and/or VEGFR-3 is used to measure the amount of VEGF-D in a sample. In such embodiments, the methods described herein comprises contacting the biological sample with VEGFR-2 and/or VEGFR-3 (or fragments thereof that bind to VEGF-D) and measuring the amount of bound VEGFR-2 and/or VEGFR-3. VEGFR-2 and VEGFR-3 are receptor tyrosine kinases that bind VEGF-D and the ligand-binding portions of the extracellular domain have been well characterized (U.S. Pat. No. 7,422,741 and International Patent Publication No. WO 2005/087808, the disclosure of which are incorporated herein by reference in their entireties). Although both receptors bind VEGF-D with high affinity, they also bind VEGF-C, a factor to consider in assay design. Thus, if VEGFR-2/VEGFR-3 is used as a capture moiety, then the sample can be pre-treated to remove VEGF-C. Alternatively, the capture of VEGF-C can be discriminated using a VEGF-D specific detection moiety, such as a VEGF-D antibody. In other variations, the VEGFR-2 or VEGFR-3 is used as a detection moiety for VEGF-D captured with an antibody. VEGFR-3 is preferred, because VEGFR-3 binds both unprocessed and partially and fully processed forms of VEGF-D.

In some embodiments, an oligonucleotide probe that hybridizes to a nucleic sequence encoding VEGF-D is used to quantify VEGF-D mRNA in a sample as a surrogate for measuring VEGF-D protein. Hybridization of the VEGF-D specific oligonucleotide probes may be detected using Northern Blot analysis, slot-blot analysis or in situ hybridization analysis and any other methods for RNA measurement known in the art, such as those techniques described in Sambrook et al. (Molecular Cloning: A Laboratory Manual, Cold Springs Harbor Laboratories (New York, 1989). Hybridization means contacting two or more nucleic acids under conditions suitable for base pairing. Hybridization includes interaction between partially or perfectly complementary nucleic acids. Suitable hybridization conditions are well known to those of skill in the art. In certain applications, it is appreciated that lower stringency conditions may be required. Under these conditions, hybridization may occur even though the sequences of the interacting strands are not perfectly complementary, being mismatched at one or more positions. Conditions may be rendered less stringent by adjusting conditions in accordance with the knowledge in the art, e.g., increasing salt concentration and/or decreasing temperature. Suitable hybridization conditions are those conditions that allow the detection of gene expression from identifiable expression units such as genes. Preferred hybridization conditions are stringent hybridization conditions, such as hybridization at 42° C. in a solution (i.e., a hybridization solution) comprising 50% formamide, 1% SDS, 1 M NaCl, 10% dextran sulfate, and washing for 30 minutes at 65° C. in a wash solution comprising 1×SSC and 0.1% SDS. It is understood in the art that conditions of equivalent stringency can be achieved through variation of temperature and buffer, or salt concentration, as described in Ausubel, et al. (Eds.), Protocols in Molecular Biology, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook, et al., (Eds.), Molecular Cloning: A Laboratory Manual, Cold Spring Harbor Laboratory Press: Cold Spring Harbor, New York (2d. Ed.; 1989), pp. 9.47 to 9.51.

The oligonucleotide probes may be labeled for detection of hybridization with the RNA extracted from the biological sample. The probes may comprise a radioactive label such as 3H, 14C, 32P, 35S, or 125I. In addition, the labels may be a fluorescent or chemiluminescent compound, such as fluorescein isothiocyanate, phycoerythrin, rhodamine, or luciferin. The labels may be enzymes such as alkaline phosphatase, β-galactosidase, biotin and avidin or horseradish peroxidase (Bayer et al., Meth. Enz., 184:138-163 (1990)). The oligonucleotide probes may be attached to solid substrates such as membranes, beads, filters, glass, silicon, metal, metal-alloy, anopore, polymeric, nylon or plastic. The substrates may be chemically treated with chemical prior to attaching probes to enhance binding or to inhibit nonspecific binding during use. Exemplary treatments include coating glass slides with coating of aminoalkyl silanes or polymeric materials such as acrylamide or proteins. The probes may be covalently or non-covalently attached to the substrate.

VEGF-D Antibodies

Antibodies that bind to VEGF-D are useful diagnostic agents for the immunodetection of the polypeptide. Exemplary VEGF-D antibodies for use in the methods described herein include those antibodies in U.S. Pat. Nos. 6,383,484; 7,410,639; and International Patent Publication No. WO 2005/087177, the disclosures of which are incorporated herein by reference in their entireties.

In general, techniques for preparing polyclonal and monoclonal antibodies as well as hybridomas capable of producing the desired antibody are well known in the art (Campbell, A. M., Monoclonal Antibodies Technology: Laboratory Techniques in Biochemistry and Molecular Biology, Elsevier Science Publishers, Amsterdam, The Netherlands (1984); St. Groth et al., J. Immunol. 35:1-21 (1990); Kohler and Milstein, Nature 256:495-497 (1975), the trioma technique, the human B-cell hybridoma technique (Kozbor et al., Immunology Today 4:72, 1983); Cole et al., in Monoclonal Antibodies and Cancer Therapy, Alan R. Liss, Inc. (1985), pp. 77-96).

Any animal (mouse, rabbit, and the like) which is known to produce antibodies can be immunized with a peptide or polypeptide of the invention. Methods for immunization are well known in the art. Such methods include subcutaneous or intraperitoneal injection of the polypeptide. One skilled in the art will recognize that the amount of the polypeptide encoded by an ORF of the invention used for immunization will vary based on the animal which is immunized, the antigenicity of the peptide and the site of injection. The protein that is used as an immunogen may be modified or administered in an adjuvant in order to increase the protein's antigenicity. Methods of increasing the antigenicity of a protein are well known in the art and include, but are not limited to, coupling the antigen with a heterologous protein (such as a globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal-antibody-producing hybridoma cells. Any one of a number of methods well known in the art can be used to identify the hybridoma cell which produces an antibody with the desired characteristics. These include screening the hybridomas with an ELISA assay, Western blot analysis, or radio-immunoassay (Lutz et al., Exp. Cell Research. 175:109-124, 1988). Hybridomas secreting the desired antibodies are cloned and the class and subclass is determined using procedures known in the art (Campbell, A. M., Monoclonal Antibody Technology: Laboratory Techniques in Biochemistry and Molecular Biology, Elsevier Science Publishers, Amsterdam, The Netherlands (1984)). Techniques described for the production of single-chain antibodies (U.S. Pat. No. 4,946, 778) can be adapted to produce single-chain antibodies to polypeptide of the invention.

For polyclonal antibodies, antibody-containing antiserum is isolated from the immunized animal and is screened for the presence of antibodies with the desired specificity using one of the above-described procedures. The invention further provides the above-described antibodies in detectably labeled form. Antibodies can be detectably labeled through the use of radioisotopes, affinity labels (such as biotin, avidin, and the like), enzymatic labels (such as horseradish peroxidase, alkaline phosphatase, and the like) fluorescent labels (such as FITC or rhodamine, and the like), paramagnetic atoms, and the like. Procedures for accomplishing such labeling are well-known in the art; for example, see Sternberger, et al., J. Histochem. Cytochem. 18:315, 1970; Bayer, et al., Meth. Enzym. 62:308, 1979; Engval, et al., Immunol. 109:129, 1972; and Goding, J. Immunol. Meth. 13:215, 1976.

The phrase "chimeric antibody," as used herein, refers to an antibody containing sequence derived from two different antibodies which typically originate from different species. Most typically, chimeric antibodies comprise variable Ig domains of a rodent monoclonal antibody fused to human constant Ig domains. Such antibodies can be generated using standard procedures known in the art (See Morrison, S. L., et al. (1984) Chimeric Human Antibody Molecules; Mouse Antigen Binding Domains with Human Constant Region Domains, Proc. Natl. Acad. Sci. USA 81, 6841-6855; and, Boulianne, G. L., et al, Nature 312, 643-646. (1984)). Although some chimeric monoclonal antibodies have proved less immunogenic in humans, the rodent variable Ig domains can still lead to a significant human anti-rodent response.

The phrase "humanized antibody" refers to an antibody derived from a non-human antibody, typically a rodent monoclonal antibody. Alternatively, a humanized antibody may be derived from a chimeric antibody. Humanized antibodies may be achieved by a variety of methods including, for example: (1) grafting the non-human complementarity determining regions (CDRs) onto a human framework and constant region (a process referred to in the art as humanizing through "CDR grafting"), or, alternatively, (2) transplanting the entire non-human variable domains, but "cloaking" them with a human-like surface by replacement of surface residues (a process referred to in the art as "veneering"). These methods are disclosed in, e.g., Jones et al., Nature 321:522 525 (1986); Morrison et al., Proc. Natl. Acad. Sci., U.S.A., 81:6851 6855 (1984); Morrison and Oi, Adv. Immunol., 44:65 92 (1988); Verhoeyer et al., Science 239:1534 1536 (1988); Padlan, Molec. Immun. 28:489 498 (1991); Padlan, Molec. Immunol. 31(3):169 217 (1994); and Kettleborough, C. A. et al., Protein Eng. 4(7):773 83 (1991) each of which is incorporated herein by reference in its entirety.

CDR grafting involves introducing one or more of the six CDRs from the mouse heavy and light chain variable Ig domains into the appropriate framework regions of a human variable Ig domain. This technique (Riechmann, L., et al., Nature 332, 323 (1988)), utilizes the conserved framework regions (FR1-FR4) as a scaffold to support the CDR loops which are the primary contacts with antigen. A significant disadvantage of CDR grafting, however, is that it can result in a humanized antibody that has a substantially lower binding affinity than the original mouse antibody, because amino acids of the framework regions can contribute to antigen binding, and because amino acids of the CDR loops can influence the association of the two variable Ig domains. To maintain the affinity of the humanized monoclonal antibody, the CDR grafting technique can be improved by choosing human framework regions that most closely resemble the framework regions of the original mouse antibody, and by site-directed mutagenesis of single amino acids within the framework or CDRs aided by computer modeling of the antigen binding site (e.g., Co, M. S., et al. (1994), J. Immunol. 152, 2968-2976).

One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region which disturb the structure of the CDRs until the predicted conformation of the humanized sequence model closely approximates the conformation of the non-human CDRs of the parent non-human antibody. Such humanized antibodies may be further derivatized to facilitate uptake and clearance, e.g., via Ashwell receptors (See, e.g., U.S. Pat. Nos. 5,530,101 and 5,585,089).

A number of humanizations of mouse monoclonal antibodies by rational design have been reported (See, for example, 20020091240 published Jul. 11, 2002, WO 92/11018 and U.S. Pat. No. 5,693,762, U.S. Pat. No. 5,766,866.

The phrase "Human Engineered™ antibody" refers to an antibody derived from a non-human antibody, typically a rodent monoclonal antibody or possibly a chimeric antibody. Human Engineering™ of antibody variable domains has been described by Studnicka [See, e.g., Studnicka et al. U.S. Pat.

No. 5,766,886; Studnicka et al. Protein Engineering 7: 805-814 (1994)] as a method for reducing immunogenicity while maintaining binding activity of antibody molecules. According to the method, each variable region amino acid has been assigned a risk of substitution. Amino acid substitutions are distinguished by one of three risk categories: (1) low risk changes are those that have the greatest potential for reducing immunogenicity with the least chance of disrupting antigen binding; (2) moderate risk changes are those that would further reduce immunogenicity, but have a greater chance of affecting antigen binding or protein folding; (3) high risk residues are those that are important for binding or for maintaining antibody structure and carry the highest risk that antigen binding or protein folding will be affected. Due to the three-dimensional structural role of prolines, modifications at prolines are generally considered to be at least moderate risk changes, even if the position is typically a low risk position.

Variable regions of the light and heavy chains of a rodent antibody can be Human Engineered™ by substituting human amino acids at positions determined to be unlikely to adversely effect either antigen binding or protein folding, but likely to reduce immunogenicity in a human environment. Although any human variable region can be used, including an individual VH or VL sequence or a human consensus VH or VL sequence or an individual or consensus human germline sequence, generally a human sequence with highest identity or homology to the rodent sequence is used to minimize the number of substitutions. The amino acid residues at any number of the low risk positions, or at all of the low risk positions, can be changed. For example, at each low risk position where the aligned murine and human amino acid residues differ, an amino acid modification is introduced that replaces the rodent residue with the human residue. In addition, the amino acid residues at any number or all of the moderate risk positions can be changed. In some embodiments, all of the low and moderate risk positions are changed from rodent to human sequence.

Synthetic genes containing modified heavy and/or light chain variable regions are constructed and linked to human γ heavy chain and/or kappa light chain constant regions. Any human heavy chain and light chain constant regions of any class or subclass may be used in combination with the Human Engineered™ antibody variable regions.

VEGF-D antibodies can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/741 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions.

Using a transgenic animal described above, an immune response can be produced to a selected antigenic molecule, and antibody producing cells can be removed from the animal and used to produce hybridomas that secrete human-derived monoclonal antibodies. Immunization protocols, adjuvants, and the like are known in the art, and are used in immunization of, for example, a transgenic mouse as described in WO 96/33735. The monoclonal antibodies can be tested for the ability to inhibit or neutralize the biological activity or physiological effect of the corresponding protein.

See also Jakobovits et al., Proc. Natl. Acad. Sci. USA, 90:2551 (1993); Jakobovits et al., Nature, 362:255-258 (1993); Bruggermann et al., Year in Immuno., 7:33 (1993); and U.S. Pat. No. 5,591,669, U.S. Pat. No. 5,589,369, U.S. Pat. No. 5,545,807; and U.S. Patent Application No. 20020199213. U.S. Patent Application No. and 20030092125 describes methods for biasing the immune response of an animal to the desired epitope. Human antibodies may also be generated by in vitro activated B cells (see U.S. Pat. Nos. 5,567,610 and 5,229,275).

The development of technologies for making repertoires of recombinant human antibody genes, and the display of the encoded antibody fragments on the surface of filamentous bacteriophage, has provided another means for generating human-derived antibodies. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference in its entirety. The antibodies produced by phage technology are usually produced as antigen binding fragments, e.g. Fv or Fab fragments, in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

Typically, the Fd fragment (VH-CH1) and light chain (VL-CL) of antibodies are separately cloned by PCR and recombined randomly in combinatorial phage display libraries, which can then be selected for binding to a particular antigen. The antibody fragments are expressed on the phage surface, and selection of Fv or Fab (and therefore the phage containing the DNA encoding the antibody fragment) by antigen binding is accomplished through several rounds of antigen binding and re-amplification, a procedure termed panning. Antibody fragments specific for the antigen are enriched and finally isolated.

Phage display techniques can also be used in an approach for the humanization of rodent monoclonal antibodies, called "guided selection" (see Jespers, L. S., et al., Bio/Technology 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., J. Mol. Biol., 227:381 (1991); Marks et al., J. Mol. Biol, 222:581-597 (1991); U.S. Pat. Nos. 5,565,332 and 5,573,905; Clackson, T., and Wells, J. A., TIBTECH 12, 173-184 (1994)). In particular, in vitro selection and evolution of antibodies derived from phage display libraries has become a powerful tool (See Burton, D. R., and Barbas III, C. F., Adv. Immunol. 57, 191-280 (1994); and, Winter, G., et al., Annu. Rev. Immunol. 12, 433-455 (1994); U.S. patent application no. 20020004215 and WO92/01047;

U.S. patent application no. 20030190317 published Oct. 9, 2003 and U.S. Pat. No. 6,054,287; U.S. Pat. No. 5,877,293.

Watkins, "Screening of Phage-Expressed Antibody Libraries by Capture Lift," Methods in Molecular Biology, Antibody Phage Display: Methods and Protocols 178: 187-193, and U.S. Patent Application Publication No. 20030044772 published Mar. 6, 2003 describes methods for screening phage-expressed antibody libraries or other binding molecules by capture lift, a method involving immobilization of the candidate binding molecules on a solid support.

"Antibody fragments" comprise a portion of an intact immunoglobulin, e.g., an antigen binding or variable region of the intact antibody, and include multi specific (bispecific, trispecific, etc.) antibodies formed from antibody fragments. Fragments of immunoglobulins may be produced by recombinant DNA techniques or by enzymatic or chemical cleavage of intact antibodies.

Nonlimiting examples of antibody fragments include Fab, Fab', F(ab')$_2$, Fv (variable region), domain antibodies (dAb, containing a VH domain) (Ward et al., Nature 341:544-546, 1989), complementarity determining region (CDR) fragments, single-chain antibodies (scFv, containing VH and VL domains on a single polypeptide chain) (Bird et al., Science 242:423-426, 1988, and Huston et al., Proc. Natl. Acad. Sci. USA 85:5879-5883, 1988, optionally including a polypeptide linker; and optionally multispecific, Gruber et al., J. Immunol. 152: 5368 (1994)), single chain antibody fragments, diabodies (VH and VL domains on a single polypeptide chain that pair with complementary VL and VH domains of another chain) (EP 404,097; WO 93/11161; and Hollinger et al., Proc. Natl. Acad. Sci. USA, 90:6444-6448 (1993)), triabodies, tetrabodies, minibodies (scFv fused to CH3 via a peptide linker (hingeless) or via an IgG hinge) (Olafsen, et al., Protein Eng Des Sel. 2004 April; 17(4):315-23), maxibodies (bivalent scFvs covalently attached to the Fc region of an immunoglobulin; Fredericks et al, Protein Engineering, Design & Selection, 17:95-106 (2004) and Powers et al., Journal of Immunological Methods, 251:123-135 (2001)); linear antibodies (tandem Fd segments (VH-CH1-VH-CH1) (Zapata et al., Protein Eng., 8(10):1057-1062 (1995)); chelating recombinant antibodies (crAb, which can bind to two adjacent epitopes on the sane antigen) (Neri et al., J Mol Biol. 246:367-73, 1995), bibodies (bispecific Fab-scFv) or tribodies (trispecific Fab-(scFv)(2)) (Schoonjans et al., J Immunol. 165:7050-57, 2000; Willems et al., J Chromatogr B Analyt Technol Biomed Life Sci. 786:161-76, 2003), intrabodies (Biocca, et al., EMBO J. 9:101-108, 1990; Colby et al., Proc Natl Acad Sci U S A. 101:17616-21, 2004) which may also comprise cell signal sequences which retain or direct the antibody intracellularly (Mhashilkar et al, EMBO J 14:1542-51, 1995; Wheeler et al., FASEB J. 17:1733-5, 2003), transbodies (cell-permeable antibodies containing a protein transduction domain (PTD) fused to scFv (Heng et al., Med Hypotheses. 64:1105-8, 2005), nanobodies (approximately 15 kDa variable domain of the heavy chain) (Cortez-Retamozo et al., Cancer Research 64:2853-57, 2004), small modular immunopharmaceuticals (SMIPs) (WO03/041600, U.S. Patent publication 20030133939 and U.S. Patent Publication 20030118592), an antigen-binding-domain immunoglobulin fusion protein, a camelized antibody (in which VH recombines with a constant region that contains hinge, CH1, CH2 and CH3 domains) (Desmyter et al., J. Biol. Chem. 276:26285-90, 2001; Ewert et al., Biochemistry 41:3628-36, 2002; U.S. Patent Publication Nos. 20050136049 and 20050037421), a VHH containing antibody, heavy chain antibodies (HCAbs, homodimers of two heavy chains having the structure H2L2), or variants or derivatives thereof, and polypeptides that contain at least a portion of an immunoglobulin that is sufficient to confer specific antigen binding to the polypeptide, such as a CDR sequence, as long as the antibody retains the desired biological activity. Such antigen fragments may be produced by the modification of whole antibodies or synthesized de novo using recombinant DNA technologies or peptide synthesis.

The term "diabodies" refers to small antibody fragments with two antigen-binding sites, which fragments comprise a heavy-chain variable domain (VH) connected to a light-chain variable domain (VL) in the same polypeptide chain (VH VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

"Single-chain Fv" or "scFv" antibody fragments comprise the VH and VL domains of antibody, wherein these domains are present in a single polypeptide chain, and optionally comprising a polypeptide linker between the VH and VL domains that enables the Fv to form the desired structure for antigen binding (Bird et al., Science 242:423-426, 1988, and Huston et al., Proc. Natl. Acad. Sci. USA 85:5879-5883, 1988). An Fd fragment consists of the VH and CH1 domains.

Additional antibody fragments include a domain antibody (dAb) fragment (Ward et al., Nature 341:544-546, 1989) which consists of a VH domain.

"Linear antibodies" comprise a pair of tandem Fd segments (VH-CH1-VH-CH1) which form a pair of antigen binding regions. Linear antibodies can be bispecific or monospecific (Zapata et al. Protein Eng. 8:1057-62 (1995)).

Functional heavy-chain antibodies devoid of light chains are naturally occurring in certain species of animals, such as nurse sharks, wobbegong sharks and Camelidae, such as camels, dromedaries, alpacas and llamas. The antigen-binding site is reduced to a single domain, the VHH domain, in these animals. These antibodies form antigen-binding regions using only heavy chain variable region, i.e., these functional antibodies are homodimers of heavy chains only having the structure H2L2 (referred to as "heavy-chain antibodies" or "HCAbs"). Camelized VHH reportedly recombines with IgG2 and IgG3 constant regions that contain hinge, CH2, and CH3 domains and lack a CH1 domain. Classical VH-only fragments are difficult to produce in soluble form, but improvements in solubility and specific binding can be obtained when framework residues are altered to be more VHH-like. (See, e.g., Reichman, et al., J Immunol Methods 1999, 231:25-38.) Camelized VHH domains have been found to bind to antigen with high affinity (Desmyter et al., J. Biol. Chem. 276:26285-90, 2001) and possess high stability in solution (Ewert et al., Biochemistry 41:3628-36, 2002). Methods for generating antibodies having camelized heavy chains are described in, for example, in U.S. Patent Publication Nos. 20050136049 and 20050037421. Alternative scaffolds can be made from human variable-like domains that more closely match the shark V-NAR scaffold and may provide a framework for a long penetrating loop structure.

Because the variable domain of the heavy-chain antibodies is the smallest fully functional antigen-binding fragment with a molecular mass of only 15 kDa, this entity is referred to as a nanobody (Cortez-Retamozo et al., Cancer Research 64:2853-57, 2004). A nanobody library may be generated from an immunized dromedary as described in Conrath et al., (Antimicrob Agents Chemother 45: 2807-12, 2001).

Intrabodies are single chain antibodies which demonstrate intracellular expression and can manipulate intracellular protein function (Biocca, et al., EMBO J. 9:101-108, 1990; Colby et al., Proc Natl Acad Sci U S A. 101:17616-21, 2004). Intrabodies, which comprise cell signal sequences which retain the antibody contruct in intracellular regions, may be produced as described in Mhashilkar et al (EMBO J 14:1542-51, 1995) and Wheeler et al. (FASEB J. 17:1733-5. 2003). Transbodies are cell-permeable antibodies in which a protein transduction domains (PTD) is fused with single chain variable fragment (scFv) antibodies Heng et al., (Med Hypotheses. 64:1105-8, 2005).

Therapeutic Methods

In another aspect, the invention provides methods of treating LAM disease. For example, the invention provides a method of treating LAM in a subject comprising diagnosing a subject as having LAM according to a method described herein; and administering a standard of care therapy to the subject. The diagnostic methods described herein may permit earlier diagnosis and therapeutic intervention than regimens that rely on conventional diagnostics.

In the context of methods of the invention, "standard of care" refers to a treatment that is generally accepted by clinicians for a certain type of patient diagnosed with a type of illness. Exemplary standard of care regimens for LAM include, but are not limited to hormone therapy (e.g., progestins, gonadotropin releasing hormone); oxygen therapy; pleurodesis; embolization, ablation or resection of angiomyolipomas; bronchodilator therapy, withdrawal from estrogen containing medications (e.g., oral contraceptives), thoracic duct ligation, oophorectomy and lung transplantation. Optionally, the method further includes one or more additional steps of measuring VEGF-D post-treatment, to monitor therapeutic efficacy of the treatment and (if warranted) adjust the dose, dosing schedule, or treatment agents.

Measuring VEGF-D concentration in a biological sample of a subject is also a useful diagnostic criterion for entering patients into therapeutic trials.

Kits

In another embodiment, kits are provided which contain the necessary reagents to carry out the assays of the present invention. In one embodiment, the invention provides a compartment kit to receive, in close confinement, one or more containers which comprises: (a) a first container comprising a VEGF-D antibody; and (b) one or more other containers comprising one or more of the following: wash reagents, reagents capable of detecting presence of a bound antibody.

In detail, a compartment kit includes any kit in which reagents are contained in separate containers. Such containers include small glass containers, plastic containers or strips of plastic or paper. Such containers allow one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibody or antibodies used in the assay, containers which contain wash reagents (such as phosphate-buffered saline, Tris buffers, and the like), and containers which contain the reagents used to detect the bound antibody or probe. Types of detection reagents include labeled nucleic acid probes, labeled secondary antibodies, or in the alternative, if the primary antibody is labeled, the enzymatic, or antibody binding reagents which are capable of reacting with the labeled antibody.

Diagnostic Systems

A "diagnostic system" is any system capable of carrying out the methods of the invention, including computing systems, environments, and/or configurations that may be suitable for use with the methods or system of the claims include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

Tests to measure and compare levels of VEGF-D can be implemented on a wide variety of diagnostic test systems. Diagnostic test systems are apparatuses that typically include means for obtaining test results from biological samples. Examples of such means include modules that automate the testing (e.g., biochemical, immunological, nucleic acid detection assays). Some diagnostic test systems are designed to handle multiple biological samples and can be programmed to run the same or different tests on each sample. Diagnostic test systems typically include means for collecting, storing and/or tracking test results for each sample, usually in a data structure or database. Examples include well-known physical and electronic data storage devices (e.g., hard drives, flash memory, magnetic tape, paper print-outs). It is also typical for diagnostic test systems to include means for reporting test results. Examples of reporting means include visible display, a link to a data structure or database, or a printer. The reporting means can be nothing more than a data link to send test results to an external device, such as a data structure, data base, visual display, or printer.

Still another embodiment of the invention is a computer readable medium having computer executable instructions for differentiating LAM from another respiratory disorder, (including TSC or a cystic or chylous lung disorder) the computer readable medium comprising: a routine, stored on the computer readable medium and adapted to be executed by a processor, to store a predetermined criterion or (predetermined criteria); and a routine stored on the computer readable medium and adapted to be executed by a processor to compare the amount of VEGF-D in a test sample data to a predetermined criterion to differentiate LAM from another respiratory disorder.

A computer-readable storage medium can comprise a data storage material encoded with computer readable data or data arrays which, when using a machine programmed with instructions for using said data, is capable of use for a variety of purposes, such as, without limitation, subject information relating to diagnostically differentiating LAM from other respiratory disorders. Measurements of VEGF-D in a sample can implemented in computer programs executing on programmable computers, comprising, inter alia, a processor, a data storage system (including volatile and non-volatile memory and/or storage elements), at least one input device, and at least one output device. Program code can be applied to input data to perform the functions described above and generate output information. The output information can be applied to one or more output devices, according to methods known in the art. The computer may be, for example, a personal computer, microcomputer, or workstation of conventional design.

Each program can be implemented in a high level procedural or object oriented programming language to communicate with a computer system. However, the programs can be implemented in assembly or machine language, if desired. The language can be a compiled or interpreted language. Each such computer program can be stored on a storage media or device (e.g., ROM or magnetic diskette or others as defined elsewhere in this disclosure) readable by a general or special purpose programmable computer, for configuring and operating the computer when the storage media or device is read by the computer to perform the procedures described herein. The health-related data management system of the invention may also be considered to be implemented as a computer-readable storage medium, configured with a computer program, where the storage medium so configured causes a computer to operate in a specific and predefined manner to perform various functions described herein. Levels of VEGF-D in a samples can then be determined and compared to a predetermined criterion as described herein. The predetermined criterion may be taken or derived from one or more subjects who have LAM, or may be taken or derived from one or more subjects who have a respiratory disorder but do not have LAM. Alternatively, the reference sample or index value or baseline value may be taken or derived from one or more healthy subjects (i.e., subjects that show no clinical manifestations of any respiratory disorder.

Figure 3:
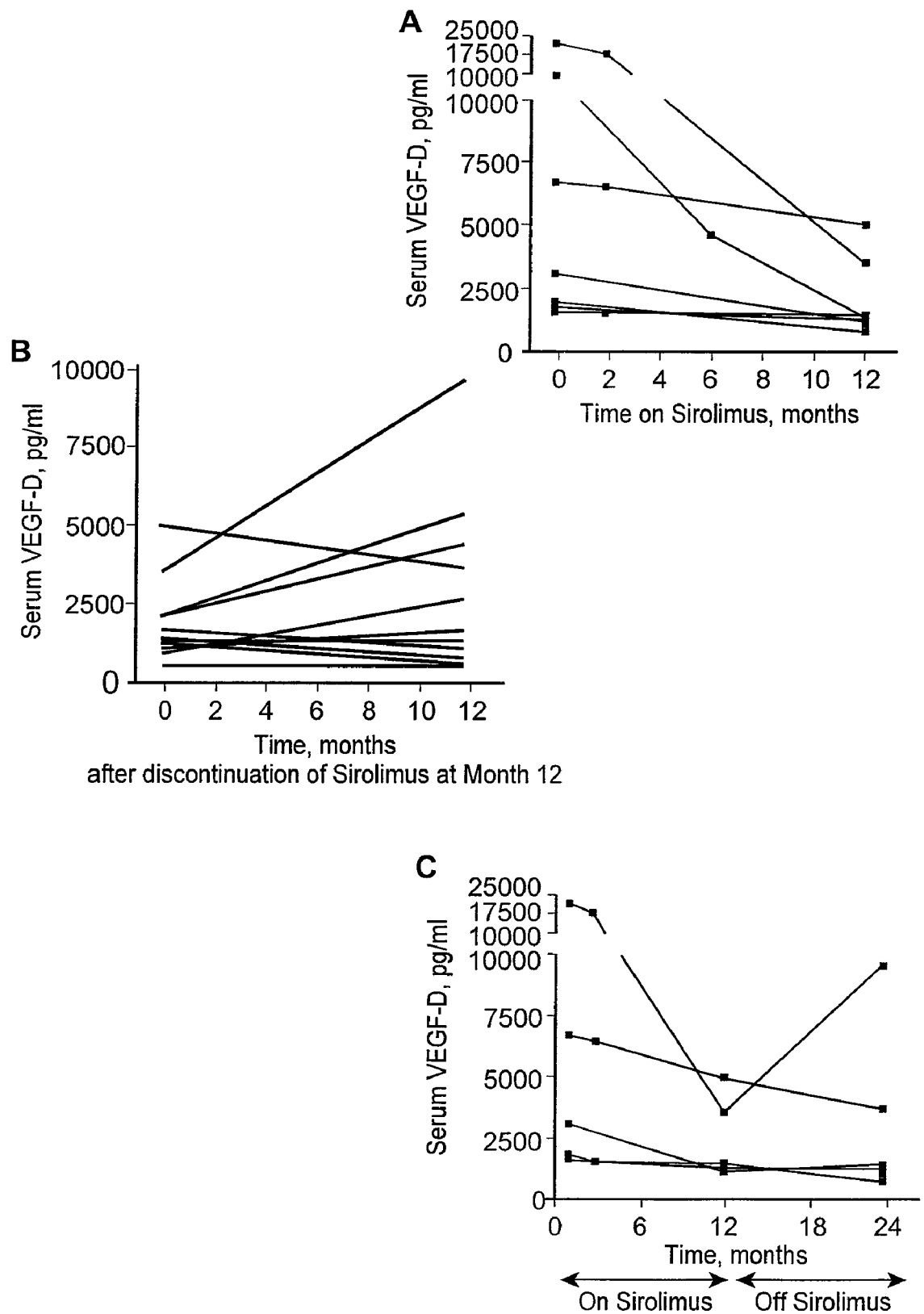
FIG. 3A shows the levels of serum VEGF-D during treatment of Sirolimus for twelve months.
FIG. 3B shows the levels of serum VEGF-D after discontinuation of Sirolimus for twelve months.
FIG. 3C shows the levels of serum VEGF-D before, during and after discontinuation of treatment with Sirolimus.

FIG. 3 illustrates an example of a suitable computing system environment 100 on which a system for the steps of the claimed method and apparatus may be implemented. The computing system environment 100 is only one example of a suitable computing environment and is not intended to suggest any limitation as to the scope of use or functionality of the method of apparatus of the claims. Neither should the computing environment 100 be interpreted as having any dependency or requirement relating to any one or combination of components illustrated in the exemplary operating environment 100.

The steps of the claimed method and system are operational with numerous other general purpose or special purpose computing system environments or configurations. Examples of well known computing systems, environments, and/or configurations that may be suitable for use with the methods or system of the claims include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like, including those systems, environments, configurations and means described elsewhere within this disclosure.

The steps of the claimed method and system may be described in the general context of computer-executable instructions, such as program modules, being executed by a computer. Generally, program modules include routines, programs, objects, components, data structures, etc. that perform particular tasks or implement particular abstract data types. The methods and apparatus may also be practiced in distributed computing environments where tasks are performed by remote processing devices that are linked through a communications network. In both integrated and distributed computing environments, program modules may be located in both local and remote computer storage media including memory storage devices.

Figure 4:
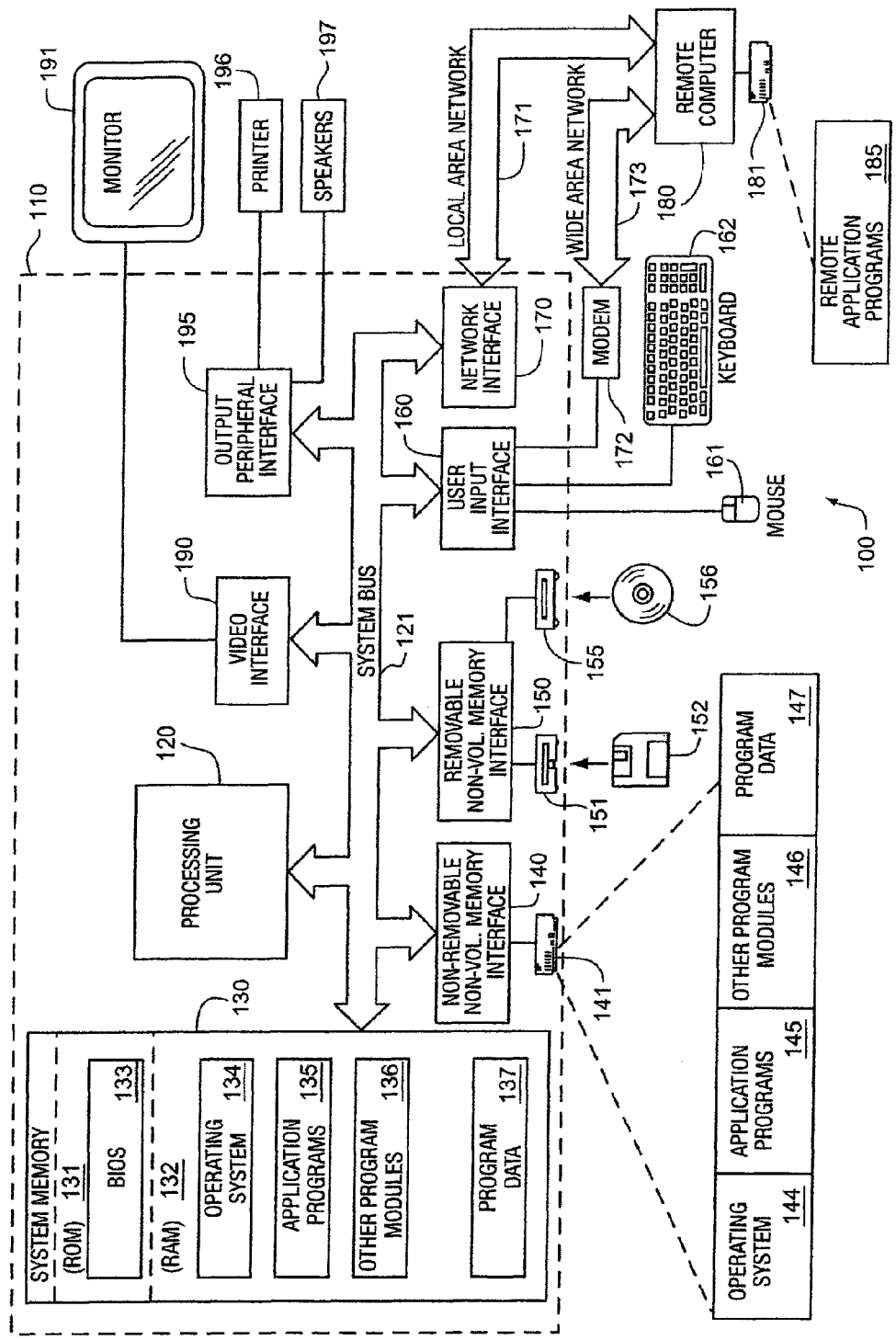
FIG. 4 illustrates an example of a suitable computing system environment 100 on which a system for the steps of the claimed method may be implemented.

With reference to FIG. 4, an exemplary system for implementing the steps of the claimed method and system includes a general purpose computing device in the form of a computer 110. Components of computer 110 may include, but are not limited to, a processing unit 120, a system memory 130, and a system bus 121 that couples various system components including the system memory to the processing unit 120. The system bus 121 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 110 typically includes a variety of computer readable media. Computer readable media can be any available media that can be accessed by computer 110 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 110. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 130 includes computer storage media in the form of volatile and/or nonvolatile memory such as read only memory (ROM) 131 and random access memory (RAM) 132. A basic input/output system 133 (BIOS), containing the basic routines that help to transfer information between elements within computer 110, such as during start-up, is typically stored in ROM 131. RAM 132 typically contains data and/or program modules that are immediately accessible to and/or presently being operated on by processing unit 120. By way of example, and not limitation, FIG. 4 illustrates operating system 134, application programs 135, other program modules 136, and program data 137.

The computer 110 may also include other removable/non-removable, volatile/nonvolatile computer storage media. By way of example only, FIG. 4 illustrates a hard disk drive 140 that reads from or writes to non-removable, nonvolatile magnetic media, a magnetic disk drive 151 that reads from or writes to a removable, nonvolatile magnetic disk 152, and an optical disk drive 155 that reads from or writes to a removable, nonvolatile optical disk 156 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 141 is typically connected to the system bus 121 through a non-removable memory interface such as interface 140, and magnetic disk drive 151 and optical disk drive 155 are typically connected to the system bus 121 by a removable memory interface, such as interface 150.

The drives and their associated computer storage media discussed above and illustrated in FIG. 4, provide storage of computer readable instructions, data structures, program modules and other data for the computer 110. In FIG. 4, for example, hard disk drive 141 is illustrated as storing operating system 144, application programs 145, other program modules 146, and program data 147. Note that these components can either be the same as or different from operating system 134, application programs 135, other program modules 136, and program data 137. Operating system 144, application programs 145, other program modules 146, and program data 147 are given different numbers here to illustrate that, at a minimum, they are different copies. A user may enter commands and information into the computer 20 through input devices such as a keyboard 162 and pointing device 161, commonly referred to as a mouse, trackball or touch pad. Other input devices (not shown) may include a microphone, joystick, game pad, satellite dish, scanner, or the like. These and other input devices are often connected to the processing unit 120 through a user input interface 160 that is coupled to the system bus, but may be connected by other interface and bus structures, such as a parallel port, game port or a universal serial bus (USB). A monitor 191 or other type of display device is also connected to the system bus 121 via an interface, such as a video interface 190. In addition to the monitor, computers may also include other peripheral output devices such as speakers 197 and printer 196, which may be connected through an output peripheral interface 190.

was aliquoted into cryotubes (250 μL). the first aliquot was stored at −20° C. for upcoming testing. The remaining aliquots were stored at −80° C. for long-term storage.

For samples obtained at a site other than the University of Cincinnati, the layer of serum above the separator gel was immediately transferred to a blue top storage tube and immediately refrigerated until shipment to Cincinnati. Upon receipt of the sample, the sample was vortexed and aliquoted as described above.

In one study, serum samples were obtained from patients with S-LAM (n=21), patients with TSC-LAM (n=17); PLCH (n=7); emphysema (n=13); lymphangiomatosis (n=7); females with TSC only (n=12), males with TSC only (n=14) and healthy controls (n=29) and evaluated by ELISA (R&D Systems) to determine the level of VEGF-D in the samples. For patients with TSC-LAM, the sample was assayed both undiluted and at 25% strength with dilution in calibrator diluent RD6P. The other samples were assayed undiluted. If a test results indicated that the amount of VEGF-d in the sample was greater than 3,000 pg/mL, the assay was repeated with sample dilution. For wash steps, a squirt bottle or manifold dispenser was used to fill the wells with wash buffers. To ensure complete removal of the liquid in the wells, the plate was inverted and blotted against clean paper towels. Results were quantified using the chromogenic substrate tetramethylbenzidine and analyzed with a microtiter plate spectrophotometer (Perkin Elmer) at 450 nm, with correction at 570 nm.

As shown in Table 1 below, VEGF-D levels were elevated up to 30-fold in LAM patients, but were normal in lymphangiomatosis, PLCH, and emphysema (FIG. 1A).

TABLE 1

| | Serum VEGF-D levels (pg/mL). | | | | | | | |
|---|---|---|---|---|---|---|---|---|
| | Healthy Controls | S-LAM | TSC-LAM | Women TSC Only | Lymphangiomatosis | PLCH | Emphysema | Sjogren's |
| n | 29 | 21 | 17 | 12 | 7 | 7 | 13 | 3 |
| Mean ± SD | 353 ± 138 | 2118 ± 2225 | 6804 ± 5791 | 491 ± 315 | 457 ± 270 | 243 ± 77 | 236 ± 74 | 240 ± 65 |
| Min. | 150 | 274 | 996 | 244 | 137 | 163 | 136 | 179 |
| Max. | 689 | 10,092 | 22,376 | 1356 | 751 | 383 | 375 | 308 |
| 95% CI | 300, 405 | 1105, 3131 | 3826, 9781 | 291, 691 | 208, 706 | 172, 314 | 191, 280 | 80, 401 |

EXAMPLES

Example 1

Serum VEGF-D is a Diagnostic Test for LAM

LAM is a rare progressive cystic lung disease of women, which occurs in the presence and absence of tuberous sclerosis complex (TSC-LAM) and sporadic or (S-LAM), respectively. The following Example demonstrates the diagnostic utility of evaluating VEGF-D levels in order to distinguish LAM from other clinically overlapping respiratory disorders.

Sample Processing and Storage: Blood was drawn using the blood draw kit provided by the Clinical Research Lab. 10 mL of blood was added to a serum separator tube and immediately inverted 8-10 times and then allowed to sit for at least 15 minutes at room temperature for proper clotting before centrifugation. The serum separator tub was then centrifuged for 10 minutes at 3500 rpm. If samples were not centrifuged within 60 minutes of the collection, then this irregularity was noted. The layer of serum above the separator gel was immediately transferred to a storage tube and vortexed. The serum A ROC curve demonstrates a highly discriminative area under the curve of 0.951 for S-LAM (FIG. 1B). Using a cut-off VEGF-D value of 574 pg/mL, test sensitivity is 86%, specificity 91%, and positive Likelihood Ratio 9.6 for S-LAM. At 750 pg/mL, specificity is 98% for S-LAM. To date, VEGF-D levels are much lower in women with TSC alone than those with TSC-LAM (p<0.001) (FIGS. 1C-1D).

Figure 2A:
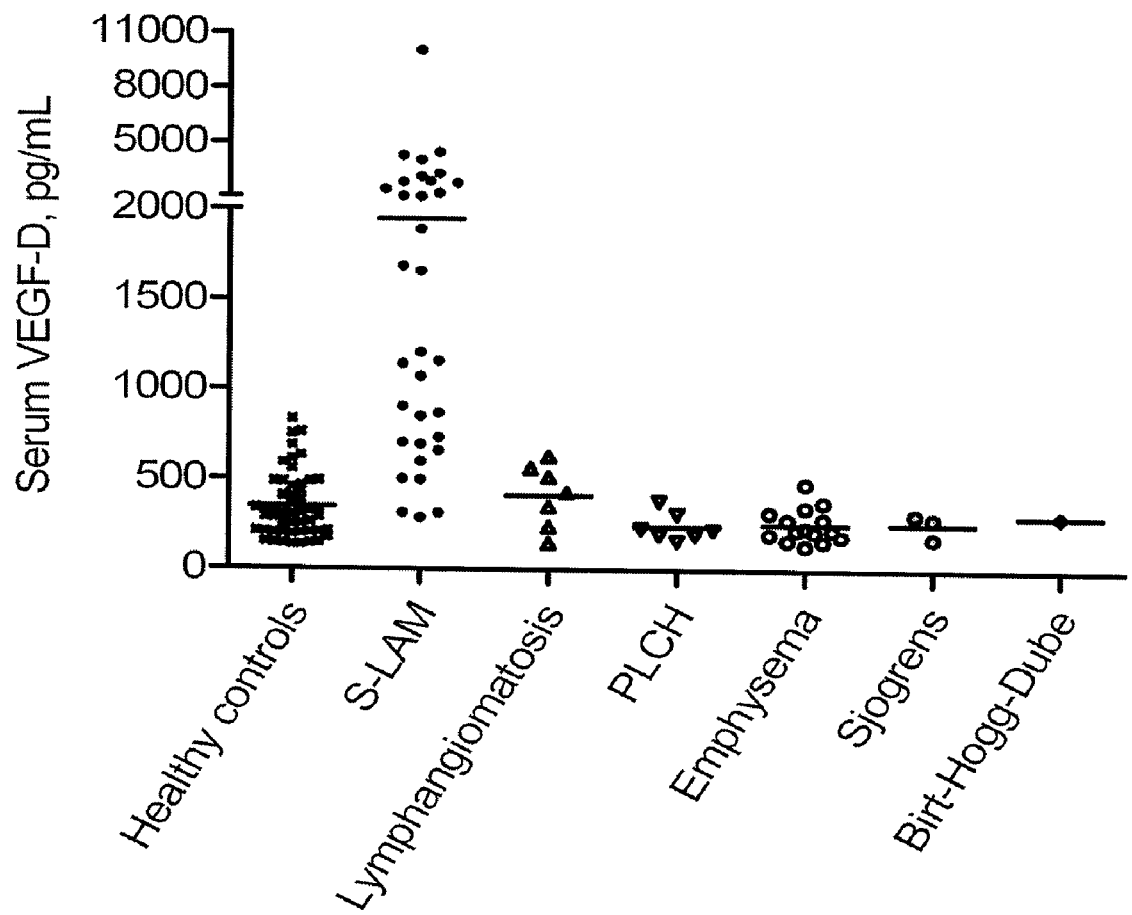
FIG. 2A shows VEGF-D serum levels in healthy controls, S-LAM patients, PLCH patients, lymphangiomatosis patients, Sjogren's syndrome patients, Birtt-Hogg-Dubé patients and emphysema patients.

In another study, serum samples were obtained from S-LAM patients (n=33) (diagnosis based on either biopsy, or cystic lung disease with AML, or chylous effusions); women diagnosed with TSC-LAM (n=20); men diagnosed with TSC-LAM (n=2); women diagnosed with TSC (without LAM) (n=14); men diagnosed with TSC (without LAM) (n=15); PLCH patients (n=7); lymphangiomatosis patients (n=7); Sjogren's syndrome with cystic lung disease patients (n=3); a Birtt-Hogg-Dubé syndrome patient (n=1); and healthy controls (n=53) and evaluated by ELISA (R&D Systems) to determine the serum VEGF-D levels in the samples. The serum VEGF-D levels are set forth in FIG. 2A. The results of the analysis are set forth below in Tables 1 and 2.

TABLE 1

Subject Characteristics

|  | Healthy Volunteer Controls | Sporadic LAM | Women, TSC-LAM | Women, TSC only | Men, TSC only | Man, TSC-LAM |
|---|---|---|---|---|---|---|
| N | 53 | 33 | 20 | 14 | 15 | 2 |
| % Female | 79.3% | 100% | 100% | 100% | 0% | 0% |
| Age, years (Mean ± SD) | 30.2 ± 5.8 | 47.6 ± 9.3 | 40.8 ± 11.9 | 29.8 ± 10 | 33.8 ± 12.9 | 53.0 ± 10 |
| FEV1 (% predicted) | | | | | | |
| Mean ± SD | N/A | 62.6 ± 23.7 | 68.7 ± 21.2 | N/A | N/A | N/A |
| Median | | 66.0 | 72.0 | | | |
| 95% Ct. | | 53.3, 72.0 | 57.7, 78.0 | | | |
| Range | | 25-106 | 25-98 | | | |

|  | Pulmonary Langerhans Cell Histiocytosis (PLCH) | Emphysema | Lymphangio-matosis | Sjoren's with cystic lung disease | Birtt-Hogg-Dubé |
|---|---|---|---|---|---|
| N | 7 | 15 | 7 | 3 | 1 |
| % Female | 42.9% | 40% | 100% | 100% | 100% |
| Age, years (Mean ± SD) | 30.4 ± 14 | 56.6 ± 14 | 40.7 ± 14.4 | 44.3 ± 4 | 58 |
| FEV1 (% predicted) | | | | | |
| Mean ± SD | 83.6 ± 6.5 | 49.0 ± 14.4 | N/A | N/A | N/A |
| Median | 85 | 48 | | | |
| 95% Ct. | 77.6, 89.5 | 38.0, 60.0 | | | |
| Range | 71-90 | 26.9-66 | | | |

TABLE 2

| VEGF-D (pg/mL) | Sensitivity | 95% CI Sensitivity | Specificity | 95% CI Specificity | Likelihood Ratio |
|---|---|---|---|---|---|
| >396 | 0.91 | 0.76-0.98 | 0.78 | 0.67-0.87 | 4.2 |
| >490 | 0.91 | 0.76-0.98 | 0.85 | 0.75-0.92 | 6.0 |
| >536 | 0.85 | 0.68-0.95 | 0.88 | 0.78-0.94 | 6.9 |
| >595 | 0.85 | 0.68-0.95 | 0.92 | 0.83-0.97 | 10.3 |
| >631 | 0.82 | 0.65-0.93 | 0.95 | 0.87-0.98 | 14.9 |
| >758 | 0.7 | 0.51-0.84 | 0.97 | 0.90-0.997 | 25.4 |
| >797 | 0.7 | 0.51-0.84 | 0.99 | 0.93-0.9997 | 50.1 |
| >800 | 0.7 | 0.51-0854 | 1.0 | 0.95-1.000 | Definite |

Figure 2B:
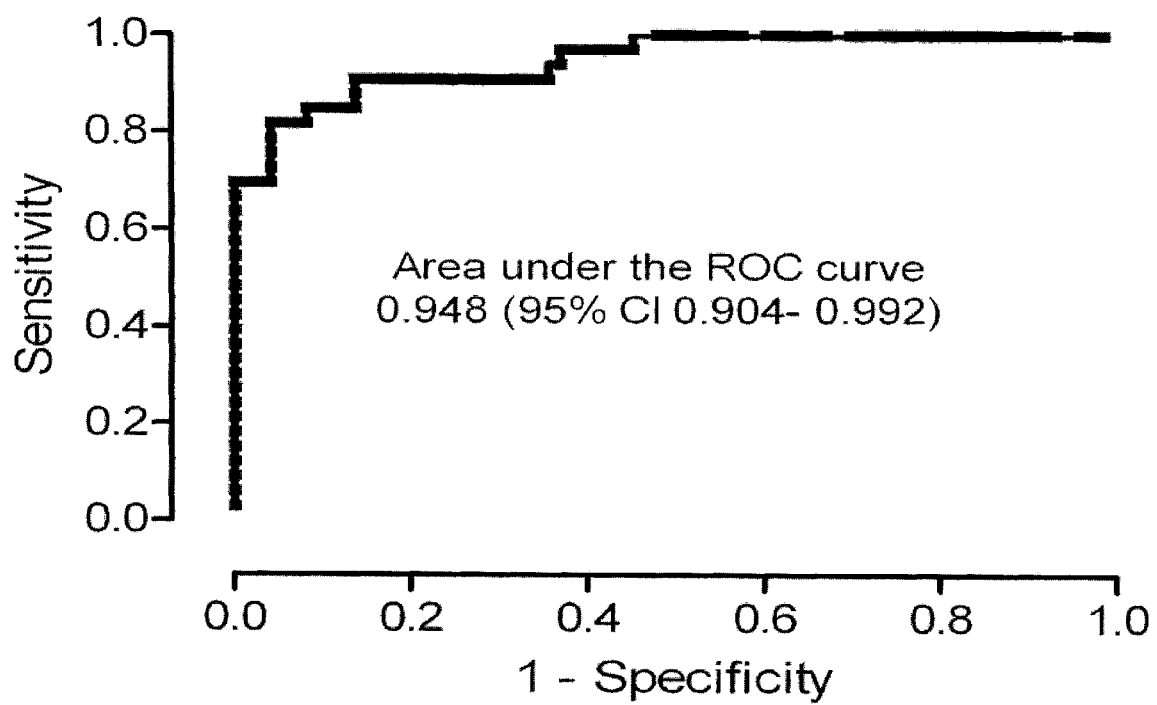
FIG. 2B shows a receiver operating characteristic (ROC) curve for VEGF-D in sporadic LAM versus healthy and other disease controls (i.e., PLCH patients, lymphangiomatosis patients, Sjogren's syndrome patients, Birtt-Hogg-Dubé patients and emphysema patients).
Figure 2C:
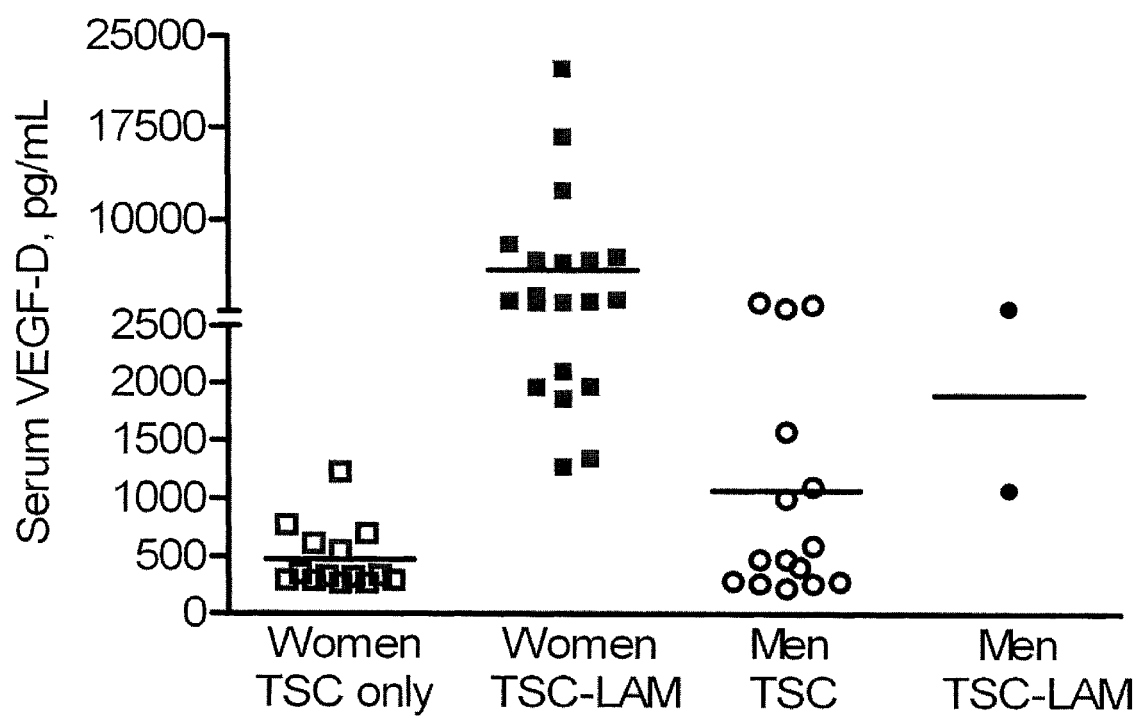
FIG. 2C shows VEGF-D serum levels in TSC-LAM, females with TSC (without LAM), males with TSC-LAM and males with TSC (without LAM).
Figure 2D:
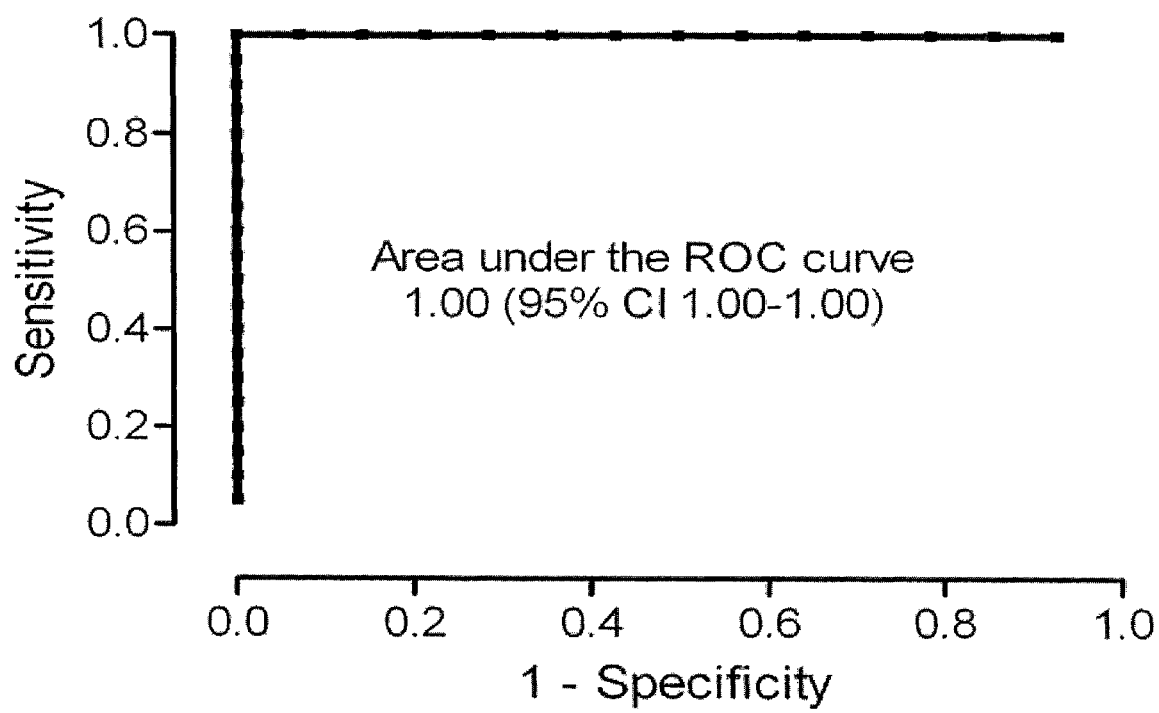
FIG. 2D shows a ROC curve for various cutoff levels of VEGF-D in differentiating between females with TSC-LAM and females with TSC (without LAM).

A ROC curve demonstrates a highly discriminative area under the curve of 0.948 for S-LAM (FIG. 2B). Using a cut-off VEGF-D value of 631 pg/mL, test sensitivity is 82%, specificity 95%, and positive Likelihood Ratio of 14.9 for S-LAM. At 758 pg/mL, specificity is 97%, and positive Likelihood Ratio of 25.4 for S-LAM. To date, VEGF-D levels are much lower in women with TSC alone than those with TSC-LAM ($p<0.001$) (FIGS. 2C-2D).

The results shown herein demonstrate that serum VEGF-D is a clinically useful diagnostic test for LAM which can distinguish S-LAM from other cystic and chylous lung diseases and TSC-LAM from TSC without cystic lung disease.

Example 2

Serum VEGF-D can be Used to Monitor Efficacy of Treatment

Serum samples were obtained from a subset of subjects before and after treatment with Sirolimus in the Cincinnati Angiomyolipoma trial (CAST). Results indicated that VEGF-D levels can be used to monitor efficacy of treatment with Sirolimus. See FIGS. 3A-3C.

What is claimed is:

1. A method of diagnosing the presence or absence of lymphangioleiomyomatosis (LAM) that permits differentiating LAM from another lung disorder comprising:
   (a) determining Vascular Endothelial Growth Factor D (VEGF-D) concentration in a biological sample from a human subject that has tuberous sclerosis complex (TSC) or a cystic or chylous lung disorder selected from the group consisting of lymphangiomatosis, Pulmonary Langerhan's cell histiocytosis (PLCH), emphysema, Sjögren's syndrome with cystic lung disease and Birtt-Hogg-Dube syndrome, and
   (b) diagnosing the presence or absence of LAM from the VEGF-D concentration, wherein elevated VEGF-D concentration in the sample, compared to VEGF-D concentration in subjects with TSC or said cystic or chylous lung disorder that are free of LAM, is diagnostic of LAM.

2. A method of diagnosing the presence or absence of LAM in a human subject comprising:
   (a) diagnosing the presence of tuberous sclerosis complex (TSC) or a cystic or chylous lung disorder selected from the group consisting of lymphangiomatosis, Pulmonary Langerhan's cell histiocytosis (PLCH), emphysema, Sjögren's syndrome with cystic lung disease and Birtt-Hogg-Dube syndrome in a human subject;

(b) determining Vascular Endothelial Growth Factor D (VEGF-D) concentration in a biological sample from said subject; and (c) diagnosing the presence or absence of LAM from the VEGF-D concentration, wherein elevated VEGF-D concentration in the sample compared to VEGF-D in subjects with TSC or said cystic or chylous lung disorder that are free of LAM, is diagnostic of LAM.

3. The method of claim 1 or 2, wherein the sample comprises serum from the subject.

4. The method of claim 1 or 2, wherein the determining VEGF-D concentration comprises contacting the biological sample from the subject with a VEGF-D antibody under conditions that allow binding of the antibody to VEGF-D in the sample.

5. The method of claim 4, wherein the determining VEGF-D concentration further comprises quantitatively determining the amount of antibody-VEGF-D complex formed.

6. The method of claim 1 or 2, wherein the human subject is female.

7. The method of claim 1 or 2, wherein the human subject has TSC.

8. The method of claim 1 or 2, wherein LAM is selected from the group consisting of tuberous sclerosis complex lymphangioleiomyomatosis (TSC-LAM) and non-heritable sporadic form lymphangioleiomyomatosis (S-LAM).

9. The method of claim 8, wherein the LAM is S-LAM.

10. The method of claim 3, wherein a serum VEGF-D concentration greater than 574 pg/ml in the biological sample is identified as elevated.

11. The method of claim 3, wherein a serum VEGF-D concentration greater than 750 pg/ml in the biological sample is identified as elevated.

12. The method of any one of claims 1-2, further comprising obtaining a computed tomography (CT) scan of a lung from the subject, wherein the diagnosing is based on the VEGF-D concentration and the CT scan.

13. The method of any one of claims 1-2, further comprising obtaining a lung biopsy, wherein the diagnosing is based on the VEGF-D concentration and the lung biopsy.

14. A method of differentiating LAM from tuberous sclerosis complex (TSC) or a cystic or chylous lung disorder comprising (a) measuring Vascular Endothelial Growth Factor D (VEGF-D) in a biological sample from a human subject having LAM or a subject free of LAM having TSC or cystic or chylous disorder selected from the group consisting of lymphangiomatosis, Pulmonary Langerhan's cell histiocytosis (PLCH) emphysema, Sjögren's syndrome and Birtt-Hogg-Dubé syndrome; and (b) differentiating LAM from TSC or said cystic or chylous lung disorder that is free of LAM by comparing the level of VEGF-D in the sample compared to the sample of predetermined criterion of free of LAM having cystic or chylous lung disorder to a predetermined criterion, wherein an elevated level of VEGF-D in the sample is diagnostic of LAM.

15. The method of claim 14, wherein the predetermined criterion is a measure of VEGF-D in humans with LAM.

16. The method of claim 14, wherein the predetermined criterion is a receiver operating characteristic curve based on data of VEGF-D measurements in subjects with LAM and subjects with TSC or a cystic or chylous lung disorder that are free of LAM.

17. The method of claim 14, wherein the predetermined criterion is a cutoff value of VEGF-D concentration, wherein the cutoff value is determined, based on previous measurements to discriminate LAM with a sensitivity and specificity calculated from measurements of VEGF-D in human subjects with LAM and human subjects with TSC or a cystic or chylous lung disorder that are free of LAM.

18. The method of claim 14, wherein the human subject free of LAM has TSC.

19. The method of claim 17, wherein the measurement of VEGF-D is a serum concentration, and the cutoff value is about 574 pg/mL.

20. The method of claim 17, wherein the measurement of VEGF-D is a serum concentration, and the cutoff value is about 750 pg/ml.

21. The method of claim 14, wherein the measuring comprises contacting the sample with a VEGF-D antibody under conditions that allow binding of the antibody to VEGF-D in the sample.

22. The method of claim 21, wherein the measuring further comprises quantitatively determining the amount of antibody-VEGF-D complex formed.

23. The method of claim 21, wherein the antibody is a monoclonal antibody.

24. The method of claim 21, wherein the antibody is immobilized on a solid support.

25. The method of claim 21, wherein an ELISA assay is used to measure the VEGF-D.

26. The method of claim 21, wherein the antibody is labeled, and the amount of VEGF-D is determined my measuring the amount of label in antibody-VEGF-D complex.

27. The method of claim 14, wherein the sample comprises serum.

28. The method of claim 14, wherein LAM is selected from the group consisting of TSC-LAM and S-LAM.

29. A method of predicting whether a human subject with TSC, or a cystic or chylous lung disorder has LAM comprising (a) measuring Vascular Endothelial Growth Factor D (VEGF-D) concentration in a biological sample from said human subject, and (b) predicting whether the subject has LAM from the VEGF-D concentration, wherein an elevated concentration of VEGF-D in the sample compared to the sample from subjects having cystic or chylous lung disorder is predictive of LAM.

* * * * *